(12) United States Patent
Bergmeister, III et al.

(10) Patent No.: US 9,914,676 B2
(45) Date of Patent: Mar. 13, 2018

(54) SELECTIVE HYDROGENATION USING A FLOW INDEX

(71) Applicant: Chevron Phillips Chemical Company LP, The Woodlands, TX (US)

(72) Inventors: Joseph Bergmeister, III, Kingwood, TX (US); Tin-Tack Peter Cheung, Kingwood, TX (US); Zongxuan Hong, Houston, TX (US); Timothy O. Odi, Kingwood, TX (US); Charles D. Nolidin, Labuan F.T. (MY); Thomas J. Gonzales, Seattle, WA (US); Jennifer L. Nill, Dickinson, TX (US); David W. Dockter, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/671,597

(22) Filed: Aug. 8, 2017

(65) Prior Publication Data
US 2017/0349507 A1 Dec. 7, 2017

Related U.S. Application Data

(62) Division of application No. 14/942,816, filed on Nov. 16, 2015, now Pat. No. 9,758,446.

(51) Int. Cl.
*B01J 19/00* (2006.01)
*B01J 19/24* (2006.01)
(Continued)

(52) U.S. Cl.
CPC .............. *C07C 5/09* (2013.01); *B01J 19/24* (2013.01); *B01J 19/245* (2013.01); *C07C 4/04* (2013.01);
(Continued)

(58) Field of Classification Search
CPC . B01J 19/00; B01J 19/24; B01J 19/245; B01J 2219/24; C07C 4/00; C07C 4/02;
(Continued)

(56) References Cited

U.S. PATENT DOCUMENTS 4,404,124 A 9/1983 Johnson et al.
4,484,015 A 11/1984 Johnson et al.
(Continued)

OTHER PUBLICATIONS

UOP Method 578-02, "Automated Pore Volume and Pore Size Distribution of Porous Substances by Mercury Porosimetry," UOP LLC, 1984, pp. 1-14.
(Continued)

*Primary Examiner* — Natasha Young
(74) *Attorney, Agent, or Firm* — Conley Rose, P.C.; Rodney B. Carroll; Chad E. Walter

(57) ABSTRACT

A process includes hydrogenating, in a reaction zone, a highly unsaturated hydrocarbon received from a hydrocarbon stream to yield a product having an unsaturated hydrocarbon, the hydrogenating step occurring in the presence of a hydrogenation catalyst which has a selectivity for conversion of the highly unsaturated hydrocarbon to the unsaturated hydrocarbon of about 90 mol % or greater based on the moles of the highly unsaturated hydrocarbon which are converted to the product, the hydrogenating step occurring in a reaction zone under conditions which include a flow index ($I_F$) in a range of about 0.09 to about 35, wherein the $I_F$ is defined as:

$$I_F = \frac{F \times [CO]}{V},$$

wherein F is the flow rate of the hydrocarbon stream into the reaction zone in units of kg/h, [CO] is the concentration of
(Continued)

carbon monoxide in the hydrocarbon stream in units of mol %, and V is the volume of the reaction zone in units of ft$^3$.

21 Claims, 2 Drawing Sheets

(51) Int. Cl.
| | |
|---|---|
| C07C 4/00 | (2006.01) |
| C07C 4/02 | (2006.01) |
| C07C 4/04 | (2006.01) |
| C07C 5/00 | (2006.01) |
| C07C 5/02 | (2006.01) |
| C07C 5/03 | (2006.01) |
| C07C 5/05 | (2006.01) |
| C10G 45/00 | (2006.01) |
| C10G 45/32 | (2006.01) |
| C10G 69/00 | (2006.01) |
| C10G 69/02 | (2006.01) |
| C10G 69/06 | (2006.01) |
| C10G 70/00 | (2006.01) |
| C10G 70/02 | (2006.01) |
| C07C 5/09 | (2006.01) |
| C10G 9/00 | (2006.01) |

(52) U.S. Cl.
CPC ................. *C07C 5/05* (2013.01); *C10G 9/00* (2013.01); *C10G 45/32* (2013.01); *C10G 69/06* (2013.01); *C10G 70/02* (2013.01); *B01J 2219/24* (2013.01); *C07C 2521/04* (2013.01); *C10G 2400/20* (2013.01); *C10G 2400/24* (2013.01)

(58) Field of Classification Search
CPC ............. C07C 4/04; C07C 5/00–5/05; C07C 2521/00–2521/04; C10G 9/00; C10G 45/00; C10G 45/32; C10G 69/00; C10G 69/02; C10G 69/06; C10G 70/00; C10G 70/02; C10G 2400/00; C10G 2400/20; C10G 2400/24
See application file for complete search history.

(56) References Cited

U.S. PATENT DOCUMENTS

| | | |
|---|---|---|
| 4,517,395 A | 5/1985 | Obenaus et al. |
| 5,475,173 A | 12/1995 | Cheung et al. |
| 5,489,565 A | 2/1996 | Cheung et al. |
| 5,510,550 A | 4/1996 | Cheung et al. |
| 5,585,318 A | 12/1996 | Johnson et al. |
| 5,587,348 A | 12/1996 | Brown et al. |
| 6,011,188 A * | 1/2000 | Crewdson ................ C07C 5/08 585/259 |
| 6,488,839 B1 * | 12/2002 | Lenglet .................... C07C 4/04 208/130 |
| 6,794,552 B2 * | 9/2004 | Cheung ................. B01J 23/002 208/144 |
| 6,858,766 B2 * | 2/2005 | Dai ....................... C10G 45/34 585/254 |
| 7,038,096 B2 | 5/2006 | Cheung et al. |
| 7,141,709 B2 | 11/2006 | Cheung et al. |
| 8,037,928 B2 * | 10/2011 | Chun .................... C10G 9/203 165/133 |
| 8,633,127 B2 | 1/2014 | Cheung et al. |
| 2002/0004622 A1 | 1/2002 | Dai et al. |
| 2004/0192983 A1 | 9/2004 | Bergmeister et al. |
| 2005/0256281 A1 | 11/2005 | Grund et al. |
| 2007/0161833 A1 | 7/2007 | Bergmeister, III et al. |
| 2010/0228065 A1 | 9/2010 | Cheung et al. |
| 2012/0209042 A1 | 8/2012 | Mamedov et al. |
| 2013/0172641 A1 | 7/2013 | Boeing et al. |
| 2017/0137346 A1 | 5/2017 | Bergmeister, III et al. |

OTHER PUBLICATIONS

Foreign communication from the related application International Application No. PCT/US2016/061849, International Search Report and Written Opinion, Feb. 1, 2017, 13 pages.

Gonzales, T. J., et al., "Chevron Phillips Chemical Company LP's Unit 24 Operating Experience with Front End E-Series Acetylene Converter Catalyst," 20th Annual Ethylene Producers' Conference, 2008, vol. 18, Session 31, 20 pages.

Gonzales, T. J., et al., "Unit 24 Operating Experience with Front End E-Series Acetylene Converter Catalyst," presentation at the AIChE Spring National Meeting, 2008, 23 pages.

Office Action dated Feb. 2, 2017 (14 pages), U.S. Appl. No. 14/942,816, filed Nov. 16, 2015.

Notice of Allowance dated Jul. 10, 2017 (12 pages), U.S. Appl. No. 14/942,816, filed Nov. 16, 2015.

Notice of Allowance dated Aug. 3, 2017 (9 pages), U.S. Appl. No. 14/942,816, filed Nov. 16, 2015.

Office Action (Restriction Requirement) dated Dec. 8, 2016 (5 pages), U.S. Appl. No. 14/942,816, filed Nov. 16, 2015.

\* cited by examiner

SELECTIVE HYDROGENATION USING A FLOW INDEX

CROSS-REFERENCE TO RELATED APPLICATIONS

This application is a divisional of and claims priority to U.S. patent application Ser. No. 14/942,816 filed Nov. 16, 2015, now U.S. Pat. No. 9,758,446, and entitled "Selective Hydrogenation Using a Flow Index," which is incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD

The present disclosure relates to the production of an unsaturated hydrocarbon, and more particularly to a hydrogenation of compounds using highly selective catalyst.

BACKGROUND

Unsaturated hydrocarbons such as ethylene and propylene are often employed as feedstocks in preparing value added chemicals and polymers. Unsaturated hydrocarbons can be produced by pyrolysis or cracking of hydrocarbons including hydrocarbons derived from coal, oil, gas, synthetic crude, naphthas, natural gas liquids, raffinate, refinery gases, ethane, propane, butane, and the like. Unsaturated hydrocarbons products produced in these manners usually contain highly unsaturated hydrocarbons such as acetylenes and diolefins that adversely affect the production of subsequent chemicals and polymers. Thus, to form an unsaturated hydrocarbon product such as a polymer grade monoolefin, the amount of acetylenes and diolefins in the monoolefin stream is typically reduced.

One technique commonly used to reduce the amount of acetylenes and diolefins in an unsaturated hydrocarbon stream primarily comprising monoolefins involves hydrogenating the acetylenes and diolefins to monoolefins. This process is selective in that hydrogenation of a monoolefin and a highly unsaturated hydrocarbon to the saturated hydrocarbon is minimized. For example, the hydrogenation of ethylene or acetylene to ethane is minimized.

One challenge to the selective hydrogenation process is the potential for a runaway reaction which is uncontrolled hydrogenation of ethylene to ethane. One methodology to minimize runaway reactions is to use a highly selective hydrogenation catalyst. The availability of highly selective hydrogenation catalysts, however, has brought about other challenges for converting a highly unsaturated hydrocarbon to an unsaturated hydrocarbon.

SUMMARY

Disclosed herein is a process comprising hydrogenating, in a reaction zone, a highly unsaturated hydrocarbon received from a hydrocarbon stream to yield a product comprising an unsaturated hydrocarbon, wherein the hydrogenating step occurs in the presence of a hydrogenation catalyst which has a selectivity for conversion of the highly unsaturated hydrocarbon to the unsaturated hydrocarbon of about 90 mol % or greater based on the moles of the highly unsaturated hydrocarbon which are converted to the product, wherein the hydrogenating step in the reaction zone occurs under conditions comprising a flow index ($I_F$) in a range of from about 0.09 to about 35; alternatively, from about 0.27 to about 25; alternatively, from about 0.4 to about 20; alternatively, from about 1.0 to about 5.6, wherein the $I_F$ is defined as:

$$I_f = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the reaction zone in units of ft$^3$.

Also disclosed herein is a system comprising a hydrocarbon stream comprising a highly unsaturated hydrocarbon and carbon monoxide, and a reaction zone receiving the hydrocarbon stream, wherein the reaction zone contains at least one hydrogenation catalyst, wherein the highly unsaturated hydrocarbon is hydrogenated in the reaction zone to yield a product comprising an unsaturated hydrocarbon, wherein the at least one hydrogenation catalyst has a selectivity for conversion of the highly unsaturated hydrocarbon to the unsaturated hydrocarbon of about 90 mol % or greater based on the moles of the highly unsaturated hydrocarbon which are converted to the product, wherein the reaction zone can comprise a flow index ($I_F$) in a range of from about 0.09 to about 35; alternatively, from about 0.27 to about 25; alternatively, from about 0.4 to about 20; alternatively, from about 1.0 to about 5.6, wherein the $I_F$ is defined as:

$$I_f = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the portion of the reaction zone in units of ft$^3$.

Further disclosed herein is a system comprising a furnace comprising at least one tube comprising a co-production metal, a cracked gas stream comprising a highly unsaturated hydrocarbon, a saturated hydrocarbon, and carbon monoxide flowing from the at least one tube, a fractionation zone comprising a deethanizer or a depropanizer, wherein the fractionation zone fractionates the cracked gas stream into an overhead product and a bottoms product, wherein the overhead product can comprise the highly unsaturated hydrocarbon, carbon monoxide, and about 90 mol % or greater of the saturated hydrocarbon contained in the cracked gas stream, a hydrocarbon stream comprising the overhead product flowing from the fractionation zone, and a reaction zone receiving the hydrocarbon stream, wherein the reaction zone can comprise at least one hydrogenation catalyst, wherein, in the reaction zone, the highly unsaturated hydrocarbon is hydrogenated to yield a product comprising an unsaturated hydrocarbon in the reaction zone, wherein the reaction zone can comprise a flow index ($I_F$) in a range of from about 0.09 to about 35; alternatively, from about 0.27 to about 25; alternatively, from about 0.4 to about 20; alternatively, from about 1.0 to about 5.6, wherein the $I_F$ is defined as:

$$I_f = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the portion of the reaction zone in units of ft$^3$.

Further disclosed herein is a process comprising cracking a feed stream to produce a cracked gas stream comprising acetylene, ethylene, ethane, methane, hydrogen, carbon monoxide, and $C_3^+$ components, fractionating the cracked gas stream into a $C_2^-$ stream and a $C_3^+$ stream, wherein the $C_2^-$ stream can comprise acetylene, ethylene, ethane, methane, hydrogen, and carbon monoxide, wherein the $C_3^+$ stream can comprise the $C_3^+$ components, hydrogenating at least a portion of the acetylene of the $C_2^-$ stream in the presence of a hydrogenation catalyst to yield a product comprising ethylene, wherein the hydrogenation catalyst has a selectivity for conversion of acetylene to ethylene of about 90 mol % or greater based on the moles of acetylene which are converted to the product, wherein the hydrogenating at least a portion of the acetylene occurs in a reaction zone under conditions comprising a flow index ($I_F$) in a range of from about 0.09 to about 35; alternatively, from about 0.27 to about 25; alternatively, from about 0.4 to about 20; alternatively, from about 1.0 to about 5.6, wherein the $I_F$ is defined as:

$$I_f = \frac{F \times [CO]}{V},$$

wherein F is the flow rate of the $C_2^-$ stream into the reaction zone in units of kg/h, [CO] is the concentration of carbon monoxide in the $C_2^-$ stream in units of mol %, and V is the volume of the portion of the reaction zone in units of ft$^3$, removing ethylene from the product, and polymerizing ethylene into one or more polymer products.

Further disclosed herein is a process comprising providing a hydrocarbon stream comprising a highly unsaturated hydrocarbon and carbon monoxide to a reaction zone comprising a hydrogenation catalyst, and hydrogenating, in the reaction zone, the highly unsaturated hydrocarbon to yield a product comprising an unsaturated hydrocarbon, wherein the hydrogenation catalyst has a selectivity for conversion of the highly unsaturated hydrocarbon to the unsaturated hydrocarbon of about 90 mol % or greater based on moles of the highly unsaturated hydrocarbon which are converted to the product, wherein the hydrogenating in the reaction zone occurs under conditions comprising a flow index ($I_F$) in a range of from about 0.09 to about 35; alternatively, from about 0.27 to about 25; alternatively, from about 0.4 to about 20; alternatively, from about 1.0 to about 5.6, wherein the $I_F$ is defined as:

$$I_f = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the portion of the reaction zone in units of ft$^3$.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Embodiments of systems and processes for selective hydrogenation using a flow index, $I_F$, are disclosed herein. It should be understood at the outset that although an illustrative implementation of one or more embodiments are provided below, the disclosed systems and processes can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

As used herein, a "highly unsaturated hydrocarbon" is defined as a hydrocarbon containing a triple bond, two conjugated carbon-carbon double bonds, or two cumulative carbon-carbon double bonds. Examples of a highly unsaturated hydrocarbon include, but are not limited to, alkynes such as acetylene, methylacetylene (also referred to as propyne), and butynes; diolefins such as propadiene, butadienes, pentadienes (including isoprene), the like, and combinations thereof.

As used herein, an "unsaturated hydrocarbon" is defined as a hydrocarbon containing an isolated carbon-carbon double bond. Examples of an unsaturated hydrocarbon include, but are not limited to, monoolefins such as ethylene, propylene, butenes, pentenes, the like, and combinations thereof.

As used herein, a "saturated hydrocarbon" is defined as a hydrocarbon containing no carbon-to-carbon double bonds or carbon-to-carbon triple bonds. Examples of a saturated hydrocarbon include, but are not limited to, methane, ethane, propane, butanes, pentanes, the like, and combinations thereof.

Figure 1:
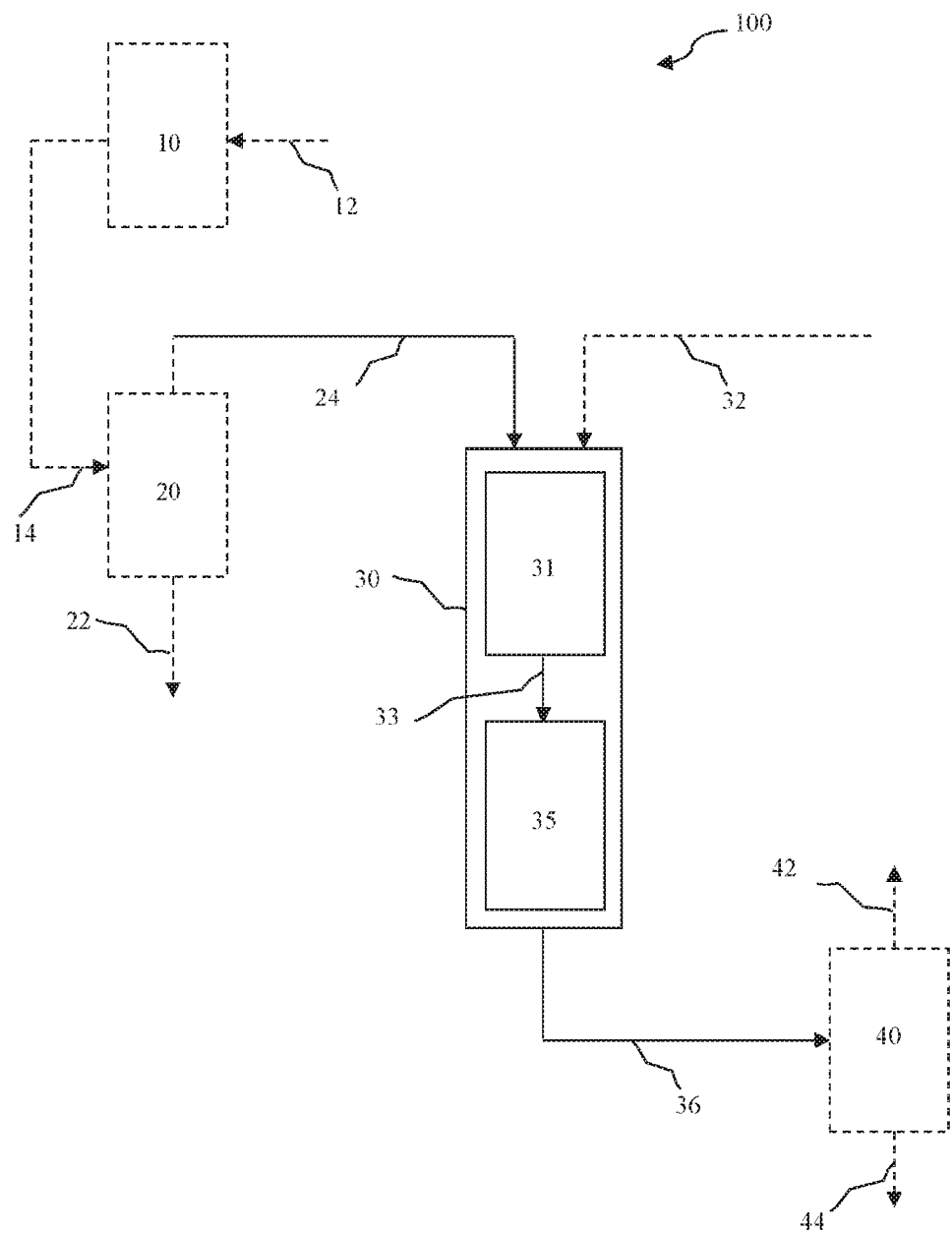
FIG. 1 illustrates embodiments of the disclosed system and process.

FIG. 1 shows embodiments of the disclosed system 100 can comprise a hydrocarbon stream 24 which flows to a reaction zone 30 (for example the reaction zone 30 receives the hydrocarbon stream 24). Generally, a highly unsaturated hydrocarbon fed to the reaction zone 30 via hydrocarbon stream 24 is hydrogenated in the reaction zone 30 in the presence of a hydrogenation catalyst and in the presence of hydrogen. In embodiments, the reaction zone 30 can comprise a first stage 31, a second stage 35 connected in series with the first stage 31, and a first effluent stream 33 via which a reaction effluent flows from the first stage 31 of the reaction zone 30 to the second stage 35 of the reaction zone 30. A highly unsaturated hydrocarbon fed to the reaction zone 30 via hydrocarbon stream 24 is hydrogenated in the first stage 31, and unconverted or unreacted highly unsaturated hydrocarbon flow in the first effluent stream 33 to the second stage 35, wherein the unconverted or unreacted highly unsaturated hydrocarbon is hydrogenated in the second stage 35. The product(s) of the first stage 31 and second stage 35 leave the reaction zone 30 via the second effluent stream 36. To accomplish hydrogenation, each of the first stage 31 and second stage 35 can comprise one or more hydrogenation catalysts (embodiments which are described herein). In an embodiment, the first stage 31, the second stage 35, or both can belong to an acetylene removal unit (ARU) of an unsaturated hydrocarbon production plant, discussed in more detail herein.

In embodiments, the reaction zone 30 can operate at conditions (for example gas phase, liquid phase, or both) effective to hydrogenate a highly unsaturated hydrocarbon to an unsaturated hydrocarbon upon contacting the disclosed hydrogenation catalyst in the presence of hydrogen. In embodiments having reaction zones with multiple stages (for example reaction zone 30 of FIG. 1), each of the first stage 31; the second stage 35; or both stages of the reaction zone 30 can operate at conditions (for example gas phase, liquid phase, or both) effective to hydrogenate the highly unsaturated hydrocarbon to an unsaturated hydrocarbon upon contacting the disclosed hydrogenation catalyst in the presence of the hydrogen.

In embodiments, the first stage 31 of the reaction zone 30 can be a first reactor, and the second stage 35 of the reaction zone 30 can be a second reactor. In such embodiments, the first reactor can be separate from and in series with the second reactor. In such embodiments, the first effluent stream 33 can comprise equipment (for example pipes, valves, pumps, heat exchangers, instrumentation, other equipment known in the art with the aid of this disclosure, or combinations thereof) which fluidly connects the first reactor and the second reactor such that a first reaction effluent can flow from the first stage 31 of the reaction zone 30 to the second stage 35 of the reaction zone 30 via the first effluent stream 33. For example, a heat exchanger can be placed between the first stage 31 of the reaction zone 30 and the second stage 35 of the reaction zone 30 to add or remove heat to achieve the reactions disclosed herein. In embodiments, no heat is added to the first effluent stream 33 between the first stage 31 and the second stage 35. In embodiments, a first temperature of the first effluent stream 33 flows into the second stage 35 (or the second reactor) is the same as or lower than a second temperature of the first effluent stream 33 as the first effluent stream 33 exits from the first stage 31 (or the first reactor).

In alternative embodiments, the first stage 31 of the reaction zone 30 can be contained within the same vessel as the second stage 35 of the reaction zone 30 (for example first stage 31 and second stage 35 are catalyst beds within the same reactor). In such embodiments, the first effluent stream 33 can comprise equipment (for example pipe, valves, baffles, packing, screens, other internal equipment known in the art with the aid of this disclosure, or combinations thereof) which fluidly connects the first stage 31 of the reaction zone 30 and the second stage 35 of the reaction zone 30 such that the reaction medium can flow from the first stage 31 of the reaction zone 30 to the second stage 35 of the reaction zone 30 (for example the first stage 31 of the reaction zone 30 and the second stage 35 of the reaction zone 30 are fluidly connected in series).

In additional or alternative embodiments, the first stage 31 of the reaction zone 30, the second stage 35 of the reaction zone 30, or both can represent a plurality of reactors. The plurality of reactors can optionally be separated by a means to remove add or remove heat produced by the reaction. The plurality of reactors can optionally be separated by a means to control inlet and effluent flows from reactors or heat removal means allowing for individual or alternatively groups of reactors within the plurality of reactors to be regenerated. The plurality of reactors can optionally be separated by equipment (for example pipe, valves, pumps, heat exchangers, instrumentation, other equipment known in the art with the aid of this disclosure, or combinations thereof).

In the various embodiments of the reaction zone 30, at least one embodiment of the hydrogenation catalyst can be arranged in any suitable configuration within the first stage 31 of the reaction zone 30; the second stage 35; or both stages of the reaction zone 30, such as a fixed catalyst bed, a fluidized bed, or both.

Designated with dashed lines in FIG. 1, the system 100 can comprise a furnace 10 comprising one or more metal tubes through which the components of the feed stream 12 flow. The tubes of the furnace 10 are configured to thermally crack at least one of the hydrocarbon components of the feed stream 12 (for example comprising a raw gas, natural gas liquids, raffinate, oil, coal oil, petroleum naphtha, a refinery stream comprising a crackable hydrocarbon, and other feed sources known in the art with the aid of this disclosure).

The product of the furnaces is a cracked gas stream 14. In embodiments, the cracked gas stream 14 can comprise a highly unsaturated hydrocarbon, an unsaturated hydrocarbon, hydrogen, carbon monoxide, a saturated hydrocarbon, or combinations thereof. In embodiments, the cracked gas stream 14 may can comprise from about 10 ppmw to about 20,000 ppmw of a highly unsaturated hydrocarbon based on the total weight of all hydrocarbons in the cracked gas stream 14.

In embodiments, the furnace 10 can comprise an insulated box and one or more burners. The components of the feed stream 12 can be heated (for example by burning of a fuel in the burner) as the components flow through the one or more tubes in the furnace 10 such that at least one component of the feed stream 12 is thermally cracked, for example, to produce an unsaturated hydrocarbon (for example ethylene, propylene, or both). At least one tube of the furnace 10 can have at least a portion which can comprise a co-production metal. In embodiments, the co-production metal is a coating on the interior of the one or more tubes (for example steel tubes). In embodiments, the co-production metal can comprise chromium, aluminum, or both. The chromium can be added to the base metal (for example steel) and migrate to form a coating on the interior of the tubes, the chromium can be coated on the interior of the tubes (for example steel tubes), or both. The aluminum can be added to the base metal (for example steel) and migrate to form a coating on the interior of the tubes, the aluminum can be coated on the interior of the tubes (for example steel tubes), or both. For example, one or more steel tubes can be aluminized with a coating of aluminum by adding aluminum to the bulk of the steel. When the one or more tubes are put into service, the aluminum migrates to the surface of the tubes to form a thin aluminized coating.

Designated with dashed lines in FIG. 1, embodiments of the system 100 can include a fractionation zone 20 which is upstream of the reaction zone 30. In embodiments, the fractionation zone 20 can comprise a vessel having internal components such as distillation trays (for example sieve-type, dual-flow, bubble cap, donut), packing materials, or both. The fractionation zone 20 can operate at conditions which provide for the fractionation of the cracked gas stream 14 according to the embodiments disclosed herein.

In embodiments, the fractionation zone 20 can comprise a deethanizer (the system 100 is in a frontend deethanizer configuration), a depropanizer (the system 100 is in a frontend depropanizer configuration), or both a demethanizer and a deethanizer (the system 100 is in a backend configuration).

The fractionation zone 20 comprising a deethanizer can receive a cracked gas stream 14 from an unsaturated hydrocarbon production process (for example from the furnace 10) and fractionate the cracked gas stream 14 into an overhead product (for example a $C_2^-$ stream) and a bottoms product (for example a $C_3^+$ stream). In such embodiments, the cracked gas stream 14 can comprise hydrogen, carbon monoxide, propane, ethane, methane, methylacetylene, propadiene, acetylene, ethylene, propylene, $C_4^+$ components (for example $C_4$ hydrocarbons and heavier), or combinations thereof. The overhead product can be an ethane-rich stream; the overhead product can comprise about 90 mol % or greater of the ethane contained in the cracked gas stream 14; the overhead product can comprise $C_2^-$ components such as acetylene, ethylene, ethane, methane, hydrogen, carbon monoxide, or combinations thereof or combinations thereof. In embodiments, the overhead product can be fed to the first stage 31 of reaction zone 30, the second stage 35 of reaction zone 30, or both, via one or more streams such as hydrocarbon stream 24. The bottoms product (for example comprising $C_3^+$ components such as propane, methylacetylene, propadiene, propylene, or combinations thereof) can flow from the fractionation zone 20 via stream 22.

The fractionation zone 20 comprising a depropanizer can receive a cracked gas stream 14 from an unsaturated hydrocarbon production process (for example from the furnace 10) and fractionate the cracked gas stream 14 into an overhead product (for example a $C_3^-$ stream) and a bottoms product (for example a $C_4^+$ stream). In such embodiments, the cracked gas stream 14 can comprise hydrogen, carbon monoxide, propane, ethane, methane, methylacetylene, propadiene, acetylene, ethylene, propylene, $C_4^+$ components (for example $C_4$ hydrocarbons and heavier), or combinations thereof. The overhead product can comprise about 90 mol % or greater of the ethane or propane contained in the cracked gas stream 14. The overhead product (for example comprising $C_3^-$ components such as hydrogen, carbon monoxide, propane, ethane, methane, methylacetylene, propadiene, acetylene, ethylene, propylene, or combinations thereof) can be fed to the first stage 31 of reaction zone 30, the second stage 35 of reaction zone 30, or both, via one or more streams such as hydrocarbon stream 24. The bottoms product (for example comprising $C_4^+$ components such as $C_4$ hydrocarbons and heavier) can flow from the fractionation zone 20 via stream 22.

In embodiments, the fractionation zone 20 can comprise a demethanizer and a deethanizer. In such an embodiment, the demethanizer can receive a cracked gas stream 14 from an unsaturated hydrocarbon production process (for example from the furnace 10) and fractionate the cracked gas stream 14 into an overhead product (for example a methane-rich stream) and a bottoms product (for example a $C_2^+$ stream). In such embodiments, the cracked gas stream 14 to the demethanizer can comprise hydrogen, carbon monoxide, propane, ethane, methane, methylacetylene, propadiene, acetylene, ethylene, propylene, $C_4^+$ components (for example $C_4$ hydrocarbons and heavier), or combinations thereof. The overhead product of the demethanizer can comprise methane, hydrogen, and carbon monoxide; can comprise about 90 mol % or greater of the methane contained in the cracked gas stream 14; or both. The bottoms product of the demethanizer can comprise about 90 mol % or greater of the ethane contained in the cracked gas stream 14; the bottoms product of the demethanizer can comprise $C_2^+$ components (for example ethane, acetylene, ethylene, methylacetylene, propadiene, propylene, propane, or combinations thereof); or combinations thereof. The bottoms product of the demethanizer then flows to the deethanizer where the deethanizer fractionates the demethanizer bottoms product into an overhead product (for example a $C_2^-$ stream) and a bottoms product (for example a $C_3^+$ stream). The overhead product of the deethanizer can be an ethane-rich stream; the overhead product of the deethanizer can comprise about 90 mol % or greater of the ethane contained in the demethanizer bottoms product; the overhead product can comprise $C_2^-$ components such as acetylene, ethylene, ethane, methane, or combinations thereof; or combinations thereof. In embodiments, the overhead product of the deethanizer can be fed to the first stage 31 of reaction zone 30, the second stage 35 of reaction zone 30, or both, via one or more streams such as hydrocarbon stream 24. The bottoms product of the deethanizer (for example comprising $C_3^+$ components such as propane, methylacetylene, propadiene, propylene, or combinations thereof) can flow from the fractionation zone 20 via stream 22.

It is understood that first stage 31 and second stage 35 of the reaction zone 30, and likewise the hydrogenation catalysts disclosed herein, are not limited to use in raw gas, frontend deethanizer, frontend depropanizer, or backend configurations, and can be used in any process wherein a highly unsaturated hydrocarbon contained within the hydrocarbon stream 24 are hydrogenated to an unsaturated hydrocarbon.

In an embodiment, the first stage 31, the second stage 35, or both can belong to an acetylene removal unit (ARU) of an unsaturated hydrocarbon production plant in a frontend deethanizer configuration, a frontend depropanizer configuration, or a backend configuration (described in more detail below).

In embodiments, the temperature within the reaction zone 30 (for example a portion thereof, the first stage 31, the second stage 35, or combinations thereof) can be in the range of from about 5° C. to about 300° C.; alternatively, from about 10° C. to about 250° C.; alternatively, from about 15° C. to about 200° C. In some embodiments, the pressure within the reaction zone 30 (for example a portion thereof, the first stage 31, the second stage 35, or combinations thereof) can be in the range of from about 15 (204 kPa) to about 2,000 (13,890 kPa) pounds per square inch gauge (psig); alternatively, from about 50 psig (446 kPa) to about 1,500 psig (10,443 kPa); alternatively, from about 100 psig (790 kPa) to about 1,000 psig (6,996 kPa).

In embodiments, a temperature of the first stage 31 of the reaction zone 30 can be the same or different than a temperature of the second stage 35 of the reaction zone 30. Likewise, a pressure of the first stage 31 of the reaction zone 30 can be the same or different than a pressure of the second stage 35 of the reaction zone 30.

In embodiments, the reaction zone 30 (for example at least a portion of reaction zone 30, the first stage 31, the second stage 35, etc.) can have a flow index ($I_F$) defined by the equation below:

$$I_f = \frac{F \times [CO]}{V},$$

wherein F is the flow rate of the hydrocarbon stream 24 into the reaction zone 30 in units of kg/h, [CO] is the concentration of carbon monoxide in the hydrocarbon stream 24 in units of mol %, and V is the volume of the reaction zone 30 (for example at least a portion of the reaction zone 30, the first stage 31, the second stage 35, etc.) in units of ft$^3$. In embodiments, the flow index ($I_F$) can comprise values in a range of from about 0.09 to about 35; alternatively, from about 0.27 to about 25; alternatively, from about 0.4 to about 20; alternatively, from about 1.0 to about 5.6.

In embodiments, at least a portion of the reaction zone can comprise 0% to 100% of the reaction zone 30 (for example comprising a single stage reaction zone). In embodiments having one or more multi-stage reaction zones, at least a portion of the reaction zone can comprise 0% to 100% of the first stage 31 of the reaction zone 30, 0% to 100% of the second stage 35 of the reaction zone 30, 0% to 100% of any other stage, or combinations thereof.

The flow index ($I_F$) values disclosed herein are attainable for the hydrogenation of a highly unsaturated hydrocarbon to an unsaturated hydrocarbon on a commercial scale using an embodiment of the hydrogenation catalyst disclosed herein. Table 1 shows some example operating conditions which achieve the flow index ($I_F$) disclosed herein:

TABLE 1

| | Volume (ft3) | Flow Rate (kg/hr) | [CO] (mol %) | Flow Index ($I_F$) [(kg mol %)/(hr ft$^3$)] |
|---|---|---|---|---|
| 1 | 500 | 65,000 | 0.04 | 5.2 |
| 2 | 500 | 85,000 | 0.15 | 25 |
| 3 | 1,000 | 225,000 | 0.012 | 2.7 |
| 4 | 1,000 | 275,000 | 0.02 | 5.5 |
| 5 | 2,000 | 77,000 | 0.007 | 0.27 |
| 6 | 2,000 | 325,000 | 0.012 | 1.95 |
| 7 | 3,000 | 425,000 | 0.008 | 1.1 |
| 8 | 3,000 | 500,000 | 0.025 | 4.2 |

As can be seen in Table 1, various reactor volumes, flow rates, and concentrations of carbon monoxide can be used which achieve the flow index disclosed herein. Reaction zone 30 of commercial reactors can be any volume, for example, ranging from 500 ft$^3$ or smaller to 3,000 ft$^3$ (as shown in Table 1) or larger. Reaction zone flow rates can be of any value, for example, ranging from 65,000 kg/hr or less to 500,000 kg/hr or more (as shown in Table 1). The concentration of carbon monoxide, [CO], can be in the ranges disclosed herein, for example, ranging from about 0.0001 mol % to about 0.15 mol %; alternatively, ranging from about 0.001 mol % to about 0.15 mol % (as shown in Table 1) or less.

It is understood the disclosed embodiments can comprise various other value combinations of volume (V), flow rate (F), and carbon monoxide concentrations [CO] which, when combined provide a flow index ($I_F$) in the ranges disclosed herein.

After hydrogenation in the reaction zone 30, the produced unsaturated hydrocarbon can be further processed; for example, in a fractionation zone 40 (designated with a dashed line) which is downstream of the reaction zone 30 and which can receive the second effluent stream 36 from the second reaction zone 35. The fractionation zone 40 (for example a downstream fractionation zone) can separate the second effluent stream 36 into a saturated hydrocarbon stream 42 (designated with a dashed line) and an unsaturated hydrocarbon stream 44 (also designated with a dashed line). In such embodiments, the fractionation zone 40 can split (in other words separate) an unsaturated hydrocarbon (for example ethylene, propylene) from a saturated hydrocarbon (for example ethane, propane) which is received from the second reaction zone 35 via second effluent stream 36. Unsaturated hydrocarbon (for example ethylene, propylene) in stream 44 can be used in a polymerization process for the production of one or more polymer products. In embodiments of system 100 in a frontend deethanizer configuration, the downstream fractionation zone 40 can operate at conditions (for example temperatures and pressures) which separate components of the second effluent stream 36 such that an unsaturated hydrocarbon can be separated from a saturated hydrocarbon. The downstream fractionation zone 40 can comprise a vessel in which a suitable technique can be used to separate the unsaturated hydrocarbon and saturated hydrocarbon.

In embodiments, the system 100 can additionally comprise any equipment associated with hydrogenation processes, such as but not limited to, one or more pumps, one or more control devices, one or more measurement instruments (for example thermocouples, transducers, analyzers, and flow meters), one or more alternative inlet lines, one or more outlet lines, one or more valves, one or more reboilers, one or more condensers, one or more accumulators, one or more tanks, one or more filters, one or more compressors, one or more dryers, or combinations thereof.

In embodiments, the hydrocarbon stream 24 can comprise a highly unsaturated hydrocarbon, an unsaturated hydrocarbon, a saturated hydrocarbon, hydrogen, carbon monoxide, or combinations thereof.

In embodiments, a hydrogen stream 32 can feed to the reaction zone 30. In reaction zone 30 embodiments having multiple stages, hydrogen can feed to the first stage 31 of the reaction zone 30, to the second stage 35 of the reaction zone 30, or both. In embodiments having hydrogen stream 32, the hydrocarbon stream 24 and hydrogen stream 32 can be combined in a single stream that is fed to the reaction zone 30 (for example to the first stage 31 in embodiments having multiple stages).

In embodiments, carbon monoxide can be contained in the feed to the reaction zone 30 (for example the first stage 31, second stage 35, or both in embodiments having multiple stages) via a separate stream. In embodiments, carbon monoxide can feed to the reaction zone 30 (for example the first stage 31, second stage 35, or both in embodiments having multiple stages) by combining a separate stream comprising carbon monoxide with a stream such as hydrocarbon stream 24, hydrogen stream 32, or both. In embodiments, carbon monoxide can feed to the reaction zone 30 (for example the first stage 31, second stage 35, or both in embodiments having multiple stages) via both a separate stream comprising carbon monoxide; and a separate stream comprising carbon monoxide combined with a stream such as hydrocarbon stream 24, hydrogen stream 32, or both. In an embodiment, the amount of carbon monoxide in the reaction zone 30 can range from about 0.0001 mol % to about 0.15 mol % based on the total moles of fluid in the reaction zone 30.

The reactive and inert components within the first stage 31, or second stage 35, or both stages of the reaction zone 30 can collectively be referred to as a reaction medium. The amount (for example moles, weight, mass, flow, concentration, described in units of mol %, wt. %, mole ratio, or other means for determining concentration, other indicator of amount, or combinations thereof) of the components of the reaction medium within the first stage 31 and second stage 35 can change over time and can depend on the location of the reaction medium within the first stage 31, the second stage 35, or both stages. Generally, as hydrogenation occurs in the first stage 31, the amount of a highly unsaturated hydrocarbon in the reaction medium decreases in the first stage 31. After the reaction medium leaves the first stage 31, the amount of the highly unsaturated hydrocarbon in the reaction medium further decreases as hydrogenation occurs in the second stage 35. Conversely, as hydrogenation occurs in the first stage 31, the amount of the yielded product comprising the unsaturated hydrocarbon (and optionally saturated hydrocarbon) in the reaction medium increases in the first stage 31. After the reaction medium exits the first stage 31 in the first effluent stream 33 and flows to the second stage 35, the amount of yielded product comprising the unsaturated hydrocarbon (and optionally a saturated hydrocarbon) in the reaction medium further increases as hydrogenation occurs in the second stage 35.

In embodiments, the reaction medium, depending on its location within the system 100 can comprise an unsaturated hydrocarbon, a highly unsaturated hydrocarbon, a saturated hydrocarbon, hydrogen, carbon monoxide, or combinations thereof.

For example, within the first stage 31, the reaction medium can comprise an unsaturated hydrocarbon which is the product of the hydrogenation of the highly unsaturated hydrocarbon in the first stage 31, the unsaturated hydrocarbon which was originally contained in the hydrocarbon stream 24 and are not the product of hydrogenation in the first stage 31, those highly unsaturated hydrocarbon which was originally contained in the hydrocarbon stream 24 and are unreacted or unconverted in the first stage 31, the saturated hydrocarbon which is a side product of the hydrogenation reaction in the first stage 31, the saturated hydrocarbon which was originally contained in the hydrocarbon stream 24, hydrogen fed to the first stage 31 via stream 32 (for example in a backend configuration), hydrogen which was originally contained in the hydrocarbon stream 24 (for example in a frontend deethanizer or frontend depropanizer configuration), carbon monoxide originally contained in the hydrocarbon stream 24 (for example in a frontend deethanizer or frontend depropanizer configuration), carbon monoxide fed to the first stage 31 (for example in a backend configuration), or combinations thereof.

The first effluent stream 33 flows from the first stage 31 to the second stage 35 and can comprise a unsaturated hydrocarbon which is the product of the hydrogenation of a highly unsaturated hydrocarbon in the first stage 31, the unsaturated hydrocarbon which was originally contained in the hydrocarbon stream 24 and is not the product of hydrogenation in the first stage 31, second stage 35, or both stages, a highly unsaturated hydrocarbon which was originally contained in the hydrocarbon stream 24 and are unreacted or unconverted in the first stage 31, a saturated hydrocarbon which is a side product of the hydrogenation reaction in the first stage 31, the saturated hydrocarbon which was originally contained in the hydrocarbon stream 24, hydrogen fed to the first stage 31 via stream 32 (for example in a backend configuration), hydrogen which was originally contained in the hydrocarbon stream 24 (for example in a frontend deethanizer or frontend depropanizer configuration), carbon monoxide originally contained in the hydrocarbon stream 24 (for example in a frontend deethanizer or frontend depropanizer configuration), carbon monoxide fed to the first stage 31 (for example in a backend configuration), or combinations thereof.

Within the second stage 35, the reaction medium can comprise an unsaturated hydrocarbon which is the product of the hydrogenation of the highly unsaturated hydrocarbon in the first stage 31, an unsaturated hydrocarbon which is the product of the hydrogenation of the highly unsaturated hydrocarbon in the second stage 35, the unsaturated hydrocarbon which was originally contained in the hydrocarbon stream 24 and are not the product of hydrogenation in the first stage 31, second stage 35, or both stages, a highly unsaturated hydrocarbon which was originally contained in the hydrocarbon stream 24 and are unreacted or unconverted in the second stage 35, a saturated hydrocarbon which is a side product of the hydrogenation reaction in the first stage 31, second stage 35, or both stages, the saturated hydrocarbon which was originally contained in the hydrocarbon stream 24, hydrogen fed to the first stage 31 via stream 32 (and passed to the second stage 35) (for example in a backend configuration), hydrogen which was originally contained in the hydrocarbon stream 24 (for example in a frontend deethanizer or frontend depropanizer configuration), carbon monoxide originally contained in the hydrocarbon stream 24 (for example in a frontend deethanizer or frontend depropanizer configuration), carbon monoxide fed to the first stage 31, carbon monoxide fed to the second stage 35 (for example in a backend configuration), or combinations thereof.

The second effluent stream 36 can comprise an unsaturated hydrocarbon which is the product of the hydrogenation of the highly unsaturated hydrocarbon in the first stage 31, an unsaturated hydrocarbon which is the product of the hydrogenation of the highly unsaturated hydrocarbon in the second stage 35, the unsaturated hydrocarbon which was originally contained in the hydrocarbon stream 24 and are not the product of hydrogenation in stages 31, stage 35, or both stages, a highly unsaturated hydrocarbon which was originally contained in the hydrocarbon stream 24 and are unreacted or unconverted in the second stage 35, a saturated hydrocarbon which is side product of the hydrogenation reaction in the first stage 31, second stage 35, or both stages, the saturated hydrocarbon which was originally contained in the hydrocarbon stream 24, hydrogen fed to the first stage 31 via stream 32 (and passed to the second stage 35), hydrogen which was originally contained in the hydrocarbon stream 24, carbon monoxide originally contained in the hydrocarbon stream 24, carbon monoxide fed to the reaction zone 30 (for example, to the first stage 31, the second stage 35), or combinations thereof.

In embodiments where the highly unsaturated hydrocarbon fed to the reaction zone 30 (for example first stage 31 or first reactor of reaction zone 30) can comprise acetylene, the mole ratio of hydrogen to the acetylene being fed to the reaction zone 30 (for example first stage 31 or first reactor of reaction zone 30) can be in the range of from about 10:1 to about 3000:1; alternatively, from about 10:1 to about 2000:1; alternatively, from about 10:1 to about 1500:1; alternatively, from about 0.1:1 to about 100:1; alternatively, from about 0.1:1 to about 10:1.

In embodiments, the reaction zone 30 can comprise at least one hydrogenation catalyst. The at least one hydrogenation catalyst can comprise an embodiment of the hydrogenation catalyst disclosed herein or multiple embodiments of the hydrogenation catalyst disclosed herein.

In embodiments where reaction zone 30 is one of two or more (in other words multiple) reaction zones, reaction zone 30 can comprise an embodiment of the hydrogenation catalyst and another reaction zone can comprise the same or different embodiment of the hydrogenation catalyst, or a different hydrogenation catalyst known in the art with the aid of this disclosure. In embodiments where a reaction zone (for example reaction zone 30) has multiple stages (for example the first stage 31 of the reaction zone 30 and second stage 35 of the reaction zone 30), one of the stages (for example the first stage 31) can comprise an embodiment of the hydrogenation catalyst disclosed herein or multiple embodiments of the hydrogenation catalyst disclosed herein, and another of the stages (for example the second stage 35) can comprise the same or different embodiment of the hydrogenation catalyst, or a different hydrogenation catalyst known in the art with the aid of this disclosure.

Figure 2:
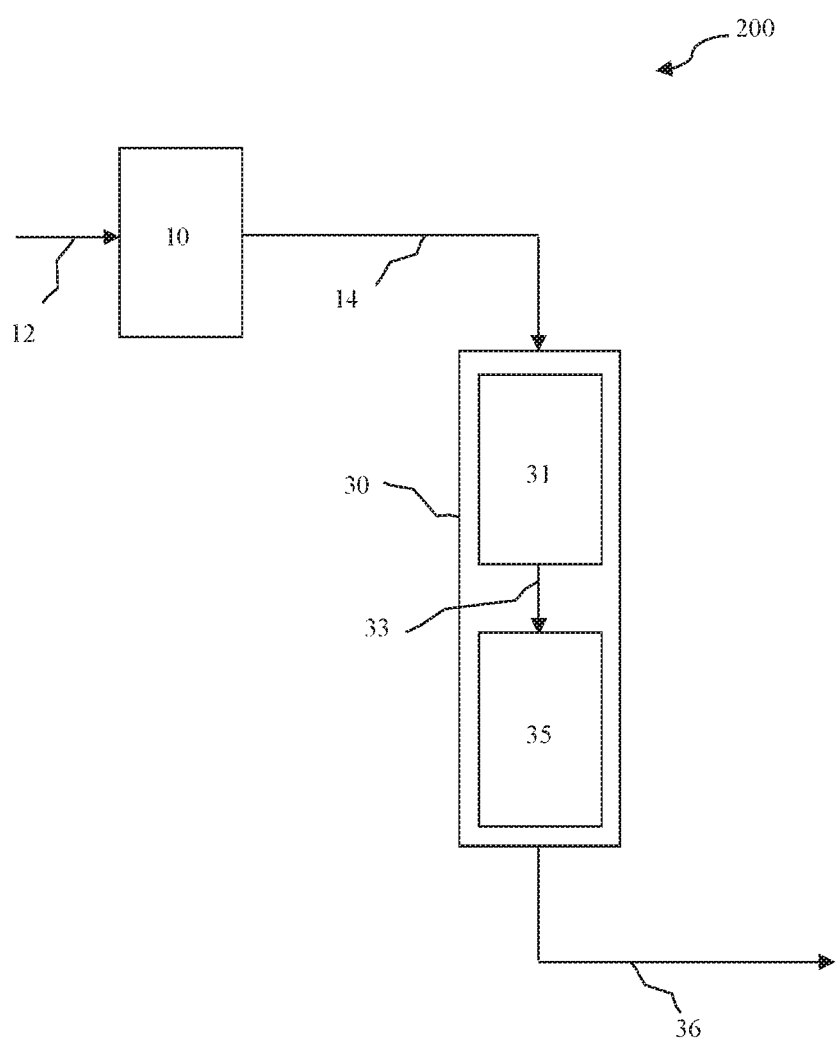
FIG. 2 illustrates other embodiments of the disclosed system and process.

FIG. 2 illustrates embodiments of the system 200 and process can include a raw gas configuration. In system 200, the reaction zone 30 can comprise one or more hydrogenation reactors (for example first stage 31 and second stage 35) that belong to an acetylene removal unit (ARU) of an unsaturated hydrocarbon production plant in a raw gas configuration. In a raw gas configuration, the cracked gas stream 14 can feed to the first stage 31, the second stage 35, or both, without first passing through a fractionation zone. In such raw gas configurations, the cracked gas stream 14 comprising hydrogen, carbon monoxide, propane, ethane, methane, methylacetylene, propadiene, acetylene, ethylene, propylene, $C_4^+$ components ($C_4^+$ components comprise $C_4$ hydrocarbons and heavier), or combinations thereof, can feed directly to the first stage 31, the second stage 35, or both. In the raw gas configuration, a highly unsaturated hydrocarbon (e.g., acetylene, methylacetylene, propadienes, butadienes, pentadienes, or combinations thereof) fed to the reaction zone 30 is hydrogenated in the first stage 31, second stage 35, or both, as described above. Components of the effluent stream 36 flowing from the reaction zone 30 may be further processed and/or separated. For example, the components in stream 36 may be separated according to techniques similar to those described above for fractionation zone 20, fraction zone 40, or both.

Embodiments of the hydrogenation catalyst described herein can generally be used for hydrogenating a highly unsaturated hydrocarbon to yield a product comprising an unsaturated hydrocarbon. For example, the hydrogenation catalyst can be contacted with at least a portion of the highly unsaturated hydrocarbon in the presence of hydrogen in a single stage reaction zone or in at least one of the first stage 31 of the reaction zone 30 and the second stage 35 of the reaction zone 30.

In embodiments, the hydrogenation catalyst can comprise any composition used for the selective hydrogenation of a highly unsaturated hydrocarbon to an unsaturated hydrocarbon which has a selectivity for conversion of the highly unsaturated hydrocarbon to an unsaturated hydrocarbon (for example ethylene) of about 90 mol %, 91 mol %, 92 mol %, 93 mol %, 94 mol %, 95 mol %, 96 mol %, 97 mol %, 98 mol %, 99 mol % or greater. Herein "selectivity" or "hydrogenation selectivity" generally refers to the amount of the highly unsaturated hydrocarbon (for example acetylene) which is converted to an unsaturated hydrocarbon (for example ethylene). For example, at a total conversion of 99 mol %, 99 moles of the highly unsaturated hydrocarbon convert to a product made of compounds such as the unsaturated hydrocarbon and saturated hydrocarbon, while one mole of the highly unsaturated hydrocarbon is unconverted or unreacted. A selectivity of 90.9 mol % to the unsaturated hydrocarbon when total conversion is at 99 mol % can indicate that, of the 99 moles of the highly unsaturated hydrocarbon which were converted to the product, 90 moles of the highly unsaturated hydrocarbon were converted to the unsaturated hydrocarbon while 9 moles of the highly unsaturated hydrocarbon were converted to other compounds such as a saturated hydrocarbon or other side products of the hydrogenation reaction.

In embodiments, the selectivity can be defined as:

$$S = 100 \times \left( \frac{UH(p) - UH(f)}{HUH(f) - HUH(p)} \right)$$

where S is selectivity in mol %, UH(p) is moles of the unsaturated hydrocarbon in the product, UH(f) is moles of the unsaturated hydrocarbon in the hydrocarbon stream 24, HUH(f) is the moles of highly unsaturated hydrocarbon in the hydrocarbon stream 24, and HUH(p) is the moles of the highly unsaturated hydrocarbon in the product.

In embodiments, the selectivity of the hydrogenation catalyst in the reaction zone 30 to an unsaturated hydrocarbon can vary. For example, the selectivity of the hydrogenation catalyst for conversion of the highly unsaturated hydrocarbon to the unsaturated hydrocarbon in the first stage 31 of the reaction zone 30 can be about 90 mol %, 91 mol %, 92 mol %, 93 mol %, 94 mol %, 95 mol %, 96 mol %, 97 mol %, 98 mol %, 99 mol % or greater, while the selectivity of the hydrogenation catalyst for conversion of the highly unsaturated hydrocarbon to the unsaturated hydrocarbon in the entire reaction zone 30 can be about 70 mol %, 75 mol %, 80 mol %, 85 mol %, 90 mol %, 91 mol %, 92 mol %, 93 mol %, 94 mol %, 95 mol %, 96 mol %, 97 mol %, 98 mol %, 99 mol % or greater.

In embodiments, the hydrogenation catalyst can comprise an inorganic support and palladium. In additional embodiments, the hydrogenation catalyst can further comprise an organophosphorus compound (for example impregnated in or on the inorganic support thereof).

In an embodiment, the inorganic support can comprise aluminas, silicas, titanias, zirconias, aluminosilicates (for example clays, ceramics, zeolites, or combinations thereof), spinels (for example zinc aluminate, zinc titanate, magnesium aluminate, or combinations thereof), or combinations thereof. In an embodiment, the support can comprise an alumina support. In some embodiments, the alumina support can comprise an alpha ($\alpha$)-alumina support or a chlorided alpha alumina support.

The inorganic support can have a surface area of from about 2 to about 100 square meters per gram ($m^2/g$); alternatively, from about 2 $m^2/g$ to about 75 $m^2/g$; alternatively, from about 3 $m^2/g$ to about 50 $m^2/g$; alternatively, from about 4 $m^2/g$ to about 25 $m^2/g$; alternatively, from about 5 $m^2/g$ to about 15 $m^2/g$; alternatively, from about 5 $m^2/g$ to about 10 $m^2/g$. The surface area of the support can be determined using any suitable method. An example of a suitable method includes the Brunauer, Emmett, and Teller ("BET") method, which measures the quantity of nitrogen adsorbed on the support. Alternatively, the surface area of the support can be measured by a mercury intrusion method such as is described in ASTM UOP 578-02, entitled "Automated Pore Volume and Pore Size Distribution of Porous Substances by MERCURY Porosimetry," which is incorporated herein by reference in its entirety.

Particles of the inorganic support generally have an average diameter of from about 1 mm to about 10 mm; alternatively, from about 1 mm to about 6 mm; alternatively, from about 2 mm to about 6 mm; alternatively, from about 3 mm to about 5 mm 9the last batch of spheres from Sasol were 2.5 to 4 mm in diameter). The inorganic support can have any suitable shape, including round or spherical (for example spheres, ellipsoidal, or combinations thereof), pellets, cylinders, granules (for example regular, irregular, or combinations thereof), extrudates (trilobe, quadrilobe, rings, wagonwheel, monoliths, or combinations thereof). Methods for shaping particles include, for example, extrusion, spray drying, pelletizing, marumerizing, agglomeration, oil drop, and the like. In an embodiment, the shape of the inorganic support can be cylindrical. In an alternative embodiment, the shape of the inorganic support can be spherical. In an alternative embodiment, the shape of the inorganic support can be an extrudate.

In an embodiment, the inorganic support can be present in an amount such that it can comprise the balance of the hydrogenation catalyst when all other components are accounted for.

In an embodiment, the hydrogenation catalyst can comprise palladium. The palladium can be added to the inorganic support by contacting the inorganic support with a palladium-containing compound to form a palladium supported catalyst as will be described in more detail later herein. Examples of suitable palladium-containing compounds include without limitation palladium chloride, palladium nitrate, ammonium hexachloropalladate, ammonium tetrachloropalladate, palladium acetate, palladium bromide, palladium iodide, tetraamminepalladium nitrate, or combinations thereof. In an embodiment, the palladium-containing compound is a component of an aqueous solution. In an embodiment, the palladium-containing compound can be a component of an acidic solution, for example an aqueous solution comprising a mineral acid. An example of palladium-containing solution suitable for use in this disclosure includes without limitation a solution comprising palladium metal.

In an embodiment, the hydrogenation catalyst can be prepared using a palladium-containing compound in an amount of from about 0.005 wt. % to about 5 wt. % based on the total weight of the hydrogenation catalyst; alternatively, from about 0.01 wt. % to about 3 wt. %; alternatively, from about 0.02 wt. % to about 1 wt. %; alternatively, from about 0.02 wt. % to about 0.5 wt. %; alternatively, from about 0.02 wt. % to about 0.1 wt. %; alternatively, from about 0.02 wt. % to about 0.04 wt. %. The amount of palladium incorporated into the hydrogenation catalyst can be in the range described herein for the amount of palladium-containing compound used to prepare the hydrogenation catalyst.

In an embodiment, the hydrogenation catalyst can further comprise an organophosphorus compound. In an embodiment, the organophosphorus compound can be represented by the general formula of $(R)_x(OR')_yP=O$; wherein x and y are integers ranging from 0 to 3 and x plus y equals 3; wherein each R can be hydrogen, a hydrocarbyl group, or combinations thereof; and wherein each R' can be a hydrocarbyl group. In some embodiments, the organophosphorus compound can include compounds such as phosphine oxides, phosphinates, phosphonates, phosphates, or combinations of any of the foregoing. For purposes of this application, the term "hydrocarbyl(s)" or "hydrocarbyl group(s)" is used herein in accordance with the definition specified by IUPAC: as a univalent group or groups derived by the removal of one hydrogen atom from a carbon atom of a "hydrocarbon." A hydrocarbyl group can be an aliphatic hydrocarbon, inclusive of acyclic and cyclic groups. A hydrocarbyl group can include rings, ring systems, aromatic rings, and aromatic ring systems. Hydrocarbyl groups can include, by way of example, aryl, alkyl, cycloalkyl, and combinations of these groups, among others. Hydrocarbyl groups can be linear or branched unless otherwise specified. For the purposes of this application, the terms "alkyl," or "cycloalkyl" refers to a univalent group derived by removal of a hydrogen atom from any carbon atom of an alkane. For the purposes of this application, the terms "aryl," or "arylene" refers to a univalent group derived by removal of a hydrogen atom from any carbon atom of an aryl ring.

In an embodiment, the hydrocarbyl group can have from 1 to 30 carbon atoms; alternatively, from 2 to 20 carbon atoms; alternatively, from 3 to 15 carbon atoms. In other embodiments, the hydrocarbyl group can have from about 6 to about 30 carbon atoms; alternatively, from about 6 to about 20 carbon atoms; alternatively, from about 6 to about 15 carbon atoms.

Generally, the alkyl group for any feature which calls for an alkyl group described herein can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,2-dimethyl-1-propyl), n-hexyl (1-hexyl) group. Persons having ordinary skill in the art with the aids of this disclosure will readily recognize which alkyl group represents primary, secondary, or tertiary alkyl groups.

Organophosphorus compounds described herein are not considered to encompass elemental phosphorus, or inorganic phosphorus compounds, except that which can be produced during the preparation of the hydrogenation catalyst described herein. Inorganic phosphorus compounds encompass monobasic, dibasic, and tribasic phosphates such as tribasic potassium phosphate ($K_3PO_4$), tribasic sodium phosphate ($Na_3PO_4$), dibasic potassium phosphate ($K_2HPO_4$), dibasic sodium phosphate ($Na_2HPO_4$), monobasic potassium phosphate ($KH_2PO_4$), and monobasic sodium phosphate ($NaH_2PO_4$). Inorganic phosphorus compounds can also encompass the corresponding phosphorus acid of above mentioned salts. Inorganic phosphorus compounds can also encompass anionic inorganic phosphorus compounds containing pentavalent phosphorus, and halogens. Examples of anionic inorganic phosphorus compounds include sodium and potassium hexafluorophosphate.

An organophosphorus compound suitable for use in this disclosure can be further characterized by a low boiling point wherein a low boiling point refers to a boiling point of about 100° C. Alternatively, an organophosphorus compound suitable for use in this disclosure can be further characterized by a high boiling point wherein a high boiling point refers to a boiling point of equal to or greater than about 100° C.

In an embodiment, the organophosphorus compound can comprise a phosphine oxide which can be represented by the general formula of $(R)_3P=O$; wherein each R can be hydrogen, a hydrocarbyl group, or combinations thereof. Examples of phosphine oxides suitable for use in this disclosure include without limitation butyldiethylphosphine oxide, butyldimethylphosphine oxide, butyldiphenylphosphine oxide, butyldipropylphosphine oxide, decyldiethylphosphine oxide, decyldimethylphosphine oxide, decyldiphenylphosphine oxide, dibutyl(2-methylphenyl)-phosphine oxide, diethyl(3-methylphenyl)-phosphine oxide, ethyldioctylphosphine oxide, ethyldibutylphosphine oxide, ethyldimethylphosphine oxide, ethyldiphenylphosphine oxide, ethyldipropylphosphine oxide, heptyldibutylphosphine oxide, heptyldiethylphosphine oxide, heptyldimethyl phosphine oxide, heptyldipentylphosphine oxide, heptyldiphenylphosphine oxide, hexyldibutylphosphine oxide, hexyldiethylphosphine oxide, hexyldimethyl phosphine oxide, hexyldipentylphosphine oxide, hexyldiphenylphosphine oxide, methylbis(4-methylphenyl)-phosphine oxide, methyldibutylphosphine oxide, methyldidecylphosphine oxide, methyldiethylphosphine oxide, methyldiphenylphosphine oxide, methyldipropylphosphine oxide, octyldimethylphosphine oxide, octyldiphenylphosphine oxide, pentyldibutylphosphine oxide, pentyldiethylphosphine oxide, pentyldimethylphosphine oxide, pentyldiphenylphosphine oxide, phenyldibutylphosphine oxide, phenyldiethylphosphine oxide, phenyldimethylphosphine oxide, phenyldipropylphosphine oxide, propyldibutylphosphine oxide, propyldimethylphosphine oxide, propyldiphenylphosphine oxide, tris(2,6-dimethylphenyl)-phosphine oxide, tris(2-methylphenyl)-phosphine oxide, tris(4-methylphenyl)-phosphine oxide, tris[4-(1,1-dimethylethyl)phenyl]-phosphine oxide, (1-methylethyl)diphenyl-phosphine oxide, 4-(diphenylmethyl)phenyl]diphenyl-phosphine oxide, bis(2-methylphenyl)(2-methylpropyl)-phosphine oxide, or combinations thereof. In some embodiments, the phosphine oxides suitable for use in this disclosure include without limitation tributylphosphine oxide, triethylphosphine oxide, triheptylphosphine oxide, trimethylphosphine oxide, trioctylphosphine oxide, tripentylphosphine oxide, tripropylphosphine oxide, triphenylphosphine oxide, or combinations thereof.

In an embodiment, the organophosphorus compound can comprise an organic phosphate which can be represented by the general formula of $(OR')_3P=O$; wherein each R' can be a hydrocarbyl group. Examples of phosphates suitable for use in this disclosure include without limitation (1-methylethyl)diphenyl phosphate, 2-ethylphenyldiphenyl phosphate, 4-(diphenylmethyl)phenyl]diphenyl phosphate, bis(2-methylphenyl)(2-methylpropyl) phosphate, butyldiethylphosphate, butyldimethylphosphate, butyldiphenylphosphate, butyldipropylphosphate, crecyldiphenylphosphate, decyldiethylphosphate, decyldimethylphosphate, decyldiphenylphosphate, dibutyl(2-methylphenyl) phosphate, diethyl(3-methylphenyl) phosphate, ethyldibutylphosphate, ethyldimethylphosphate, ethyldioctylphosphate, ethyldiphenylphosphate, ethyldipropylphosphate, heptyldibutylphosphate, heptyldiethylphosphate, heptyldimethyl phosphate, heptyldipentylphosphate, heptyldiphenylphosphate, hexyldibutylphosphate, hexyldiethylphosphate, hexyldimethyl phosphate, hexyldipentylphosphate, hexyldiphenylphosphate, methylbis(4-methylphenyl) phosphate, methyldibutylphosphate, methyldidecylphosphate, methyldiethylphosphate, methyldiphenylphosphate, methyldipropylphosphate, octyldimethylphosphate, octyldiphenylphosphate, pentyldibutylphosphate, pentyldiethylphosphate, pentyldimethylphosphate, pentyldiphenylphosphate, phenyldibutylphosphate, phenyldiethylphosphate, phenyldimethylphosphate, phenyldipropylphosphate, propyldibutylphosphate, propyldimethylphosphate, propyldiphenylphosphate, tri(2,3-dichloropropyl) phosphate, tri(2,6-dimethylphenyl) phosphate, tri(2-chloroethyl) phosphate, tri(nonylphenyl) phosphate, tris(2,6-dimethylphenyl) phosphate, tris(2-methylphenyl) phosphate, tris(4-methylphenyl) phosphate, tris[4-(1,1-dimethylethyl)phenyl] phosphate, or combinations thereof. In some embodiments, the phosphates suitable for use in this disclosure include without limitation tributylphosphate, tricresyl phosphate, tricyclohexyl phosphate, tridecylphosphate, triethylphosphate, triheptylphosphate, triisopropyl phosphate, trimethylphosphate, trioctadecyl phosphate, trioctylphosphate, tripentylphosphate, triphenylphosphate, tripropylphosphate, trixylylphosphate, or combinations thereof.

In an embodiment, the organophosphorus compound can comprise a phosphinate, which can be represented by the general formula of $(R)_2(OR')P=O$; wherein each R can be hydrogen, a hydrocarbyl group, or combinations thereof; and wherein each R' can be a hydrocarbyl group. Examples of phosphinates suitable for use in this disclosure include without limitation butyl butylphosphinate, butyl dibutylphosphinate, butyl diethylphosphinate, butyl diphenylphosphinate, butyl dipropylphosphinate, butyl ethylphosphinate, butyl heptylphosphinate, butyl hexylphosphinate, butyl pentylphosphinate, butyl phenylphosphinate, butyl propylphosphinate, decyl pentylphosphinate, butyl butylpentylphosphinate, ethyl butylphosphinate, ethyl decylphosphinate, ethyl dibutylphosphinate, ethyl diethylphosphinate, ethyl dimethylphosphinate, ethyl diphenylphosphinate, ethyl dipropylphosphinate, ethyl ethylphosphinate, ethyl heptylphosphinate, ethyl hexylphosphinate, ethyl octylphosphinate, ethyl pentylphosphinate, ethyl phenylphosphinate, ethyl propylphosphinate, heptyl dibutylphosphinates, heptyl pentylphosphinate, heptylphosphinate, hexyl dibutylphosphinate, hexyl pentylphosphinate, isopropyl diphenylphosphinate, methyl butylphosphinate, methyl decylphosphinate, methyl dibutylphosphinate, methyl diethylphosphinate, methyl dimethylphosphinate, methyl diphenylphosphinates, methyl dipropylphosphinate, methyl ethylphosphinate, methyl heptylphosphinate, methyl hexylphosphinate, methyl octylphosphinate, methyl pentylphosphinate, methyl phenylphosphinate, methyl propylphosphinate, octyl pentylphosphinate, octylphosphinate, pentyl dibutylphosphinate, pentylphosphinate, phenyl butylphosphinate, phenyl decylphosphinate, phenyl dibutylphosphinate, phenyl diethylphosphinate, phenyl diethylphosphinate, phenyl dimethylphosphinate, phenyl diphenylphosphinate, phenyl diphenylphosphinate, phenyl dipropylphosphinate, phenyl ethylphosphinate, phenyl heptylphosphinate, phenyl hexylphosphinate, phenyl octylphosphinate, phenyl pentylphosphinate, phenyl pentylphosphinate, phenyl phenylphosphinate, phenyl propylphosphinate, phenylphosphinate, propyl diphenylphosphinate, or combinations thereof.

In an embodiment, the organophosphorus compound can comprise a phosphonate, which can be represented by the general formula of $(R)(OR')_2P=O$; wherein each R can be hydrogen, a hydrocarbyl group, or combinations thereof and wherein each R' can be a hydrocarbyl group. Examples of phosphonates suitable for use in this disclosure include without limitation (1-methylethyl)diphenyl phosphonate, 2-ethylphenyldiphenyl phosphonate, 4-(diphenylmethyl)phenyl]diphenyl phosphonate, bis(2-methylphenyl)(2-methylpropyl) phosphonate, butyldiethylphosphonate, butyldimethylphosphonate, butyldiphenylphosphonate, butyldipropylphosphonate, crecyldiphenylphosphonate, decyldiethylphosphonate, decyldimethylphosphonate, decyldiphenylphosphonate, dibutyl(2-methylphenyl) phosphonate, diethyl(3-methylphenyl) phosphonate, ethyldibutylphosphonate, ethyldimethylphosphonate, ethyldioctylphosphonate, ethyldiphenylphosphonate, ethyldipropylphosphonate, heptyldibutylphosphonate, heptyldiethylphosphonate, heptyldimethyl phosphonate, heptyldipentylphosphonate, heptyldiphenylphosphonate, hexyldibutylphosphonate, hexyldiethylphosphonate, hexyldimethyl phosphonate, hexyldipentylphosphonate, hexyldiphenylphosphonate, methylbis(4-methylphenyl) phosphonate, methyldibutylphosphonate, methyldidecylphosphonate, methyldiethylphosphonate, methyldiphenylphosphonate, methyldipropylphosphonate, octyldimethylphosphonate, octyldiphenylphosphonate, pentyldibutylphosphonate, pentyldiethylphosphonate, pentyldimethylphosphonate, pentyldiphenylphosphonate, phenyldibutylphosphonate, phenyldiethylphosphonate, phenyldimethylphosphonate, phenyldipropylphosphonate, propyldibutylphosphonate, propyldimethylphosphonate, propyldiphenylphosphonate, tri(2,3-dichloropropyl) phosphonate, tri(2,6-dimethylphenyl) phosphonate, tri(2-chloroethyl) phosphonate, tri(nonylphenyl) phosphonate, tris(2,6-dimethylphenyl) phosphonate, tris(2-methylphenyl) phosphonate, tris(4-methylphenyl) phosphonate, tris[4-(1,1-dimethylethyl)phenyl]phosphonate, or combinations thereof. In some embodiments, the phosphonates suitable for use in this disclosure include without limitation tributylphosphonate, tricresyl phosphonate, tricyclohexyl phosphonate, tridecylphosphonate, triethylphosphonate, triheptylphosphonate, triisopropyl phosphonate, trimethylphosphonate, trioctadecylphosphonate, trioctylphosphonate, tripentylphosphonate, triphenylphosphonate, tripropylphosphonate, trixylylphosphonate, or combinations thereof.

In an embodiment, the hydrogenation catalyst can comprise a precursor to the organophosphorus compound. The organophosphorus compound precursor can comprise any material which can be converted to the organophosphorus compound which activates the hydrogenation catalyst under the conditions to which the hydrogenation catalyst is exposed and that is compatible with the other components of the hydrogenation catalyst. In an embodiment, the organophosphorus compound precursor can be represented by the general formula of $(R)_x(OR')_yP$; wherein x and y are integers ranging from 0 to 3 and x plus y equals 3; wherein each R can be hydrogen, a hydrocarbyl group, or combinations thereof; and wherein each R' can be a hydrocarbyl group. The organophosphorus compound precursor can include without limitation phosphines, phosphites, phosphinites, phosphonites, or combinations thereof. In an embodiment, the organophosphorus compound precursor can comprise a phosphine that can form a phosphine oxide when exposed to an oxidizing agent, temperatures greater than about 20° C., or combinations thereof. In an embodiment, the organophosphorus compound precursor can comprise a phosphite that can form a phosphate when exposed to an oxidizing agent, temperatures greater than about 20° C., or combinations thereof. In an embodiment, the organophosphorus compound precursor can comprise a phosphinite that can form a phosphinate when exposed to oxidizing agent, temperatures greater than about 20° C., or combinations thereof. In an embodiment, the organophosphorus compound precursor can comprise a phosphonite that can form a phosphonate when exposed to air, temperatures greater than about 20° C., or combinations thereof.

In an embodiment, the organophosphorus compound can comprise phosphines, which can be represented by the general formula of $(R)_3P$; wherein each R can be hydrogen, a hydrocarbyl group, or combinations thereof. Examples of phosphines suitable for use as phosphine oxide precursors in this disclosure include without limitation (1-methylethyl)diphenylphosphine, 2-ethylphenyldiphenyl phosphine, 4-(diphenylmethyl)phenyl]diphenylphosphine, bis(2-methylphenyl)(2-methylpropyl) phosphine, butyldiethylphosphine, butyldimethylphosphine, butyldiphenylphosphine, butyldipropylphosphine, crecyldiphenylphosphine, cyclohexyldiphenylphosphine, decyldiethylphosphine, decyldimethylphosphine, decyldiphenylphosphine, dibutyl(2-methylphenyl) phosphine, dicyclohexylphenylphosphine, diethyl(3-methylphenyl)phosphine, ethyldibutylphosphine, ethyldimethylphosphine, ethyldioctylphosphine, ethyldiphenylphosphine, ethyldipropylphosphine, heptyldibutylphosphine, heptyldiethylphosphine, heptyldimethyl phosphine, heptyldipentylphosphine, heptyldiphenylphosphine, hexyldibutylphosphine, hexyldiethylphosphine, hexyldimethyl phosphine, hexyldipentylphosphine, hexyldiphenylphosphine, methylbis(4-methylphenyl) phosphine, methyldibutylphosphine, methyldidecylphosphine, methyldiethylphosphine, methyldiphenylphosphine, methyldipropylphosphine, octyldimethylphosphine, octyldiphenylphosphine, pentyldibutylphosphine, pentyldiethylphosphine, pentyldimethylphosphine, pentyldiphenylphosphine, phenyldibutylphosphine, phenyldiethylphosphine, phenyldimethylphosphine, phenyldipropylphosphine, propyldibutylphosphine, propyldimethylphosphine, propyldiphenylphosphine, tri(2,3-dichloropropyl) phosphine, tri(2,6-dimethylphenyl) phosphine, tri(2-chloroethyl) phosphine, tri(nonylphenyl) phosphine, tris(2,6-dimethylphenyl) phosphine, tris(2-methylphenyl) phosphine, tris(4-methylphenyl) phosphine, tris(methoxyphenyl)phosphine, tris[4-(1,1-dimethylethyl)phenyl]phosphine, or combinations thereof. In some embodiments, the phosphines suitable for use in this disclosure include without limitation tributylphosphine, tricresyl phosphine, tricyclohexyl phosphine, tridecylphosphine, triethylphosphine, triheptylphosphine, triisopropylphosphine, trimethylphosphine, trioctadecyl phosphine, trioctylphosphine, tripentylphosphine, triphenylphosphine, tripropylphosphine, tri-t-butylphosphine, tritolylphosphine, trixylylphosphine, or combinations thereof.

In an embodiment, the organophosphorus compound can comprise phosphites, which can be represented by the general formula of $(OR')_3P$; wherein each R' can be a hydrocarbyl group. Examples of phosphites suitable for use as phosphate precursors in this disclosure include without limitation (1-methylethyl)diphenylphosphite, 2-ethylphenyldiphenyl phosphite, 4-(diphenylmethyl)phenyl]diphenylphosphite, bis(2-methylphenyl)(2-methylpropyl) phosphite, butyldiethylphosphite, butyldimethylphosphite, butyldiphenylphosphite, butyldipropylphosphite, crecyldiphenylphosphite, cyclohexyldiphenylphosphite, decyldiethylphosphite, decyldimethylphosphite, decyldiphenylphosphite, dibutyl(2-methylphenyl) phosphite, dicyclohexylphenylphosphite, diethyl(3-methylphenyl)phosphite, ethyldibutylphosphite, ethyldimethylphosphite, ethyldioctylphosphite, ethyldiphenylphosphite, ethyldipropylphosphite, heptyldibutylphosphite, heptyldiethylphosphite, heptyldimethyl phosphite, heptyldipentylphosphite, heptyldiphenylphosphite, hexyldibutylphosphite, hexyldiethylphosphite, hexyldimethyl phosphite, hexyldipentylphosphite, hexyldiphenylphosphite, methylbis(4-methylphenyl) phosphite, methyldibutylphosphite, methyldidecylphosphite, methyldiethylphosphite, methyldiphenylphosphite, methyldipropylphosphite, octyldimethylphosphite, octyldiphenylphosphite, pentyldibutylphosphite, pentyldiethylphosphite, pentyldimethylphosphite, pentyldiphenylphosphite, phenyldibutylphosphite, phenyldiethylphosphite, phenyldimethylphosphite, phenyldipropylphosphite, propyldibutylphosphite, propyldimethylphosphite, propyldiphenylphosphite, tri(2-chloroethyl) phosphite, tri(nonylphenyl) phosphite, tris(2,3-dichloropropyl) phosphite, tris(2,6-dimethylphenyl) phosphite, tris (2-methylphenyl) phosphite, tris(4-methylphenyl) phosphite, tris(methoxyphenyl)phosphite, tris[4-(1,1-dimethylethyl)phenyl]phosphite, tri-t-butylphosphite, or combinations thereof. In some embodiments, the phosphites suitable for use in this disclosure include without limitation tributylphosphite, tricresyl phosphite, tricyclohexyl phosphite, tridecylphosphite, triethylphosphite, triheptylphosphite, triisopropylphosphite, trimethylphosphite, trioctadecyl phosphite, trioctylphosphite, tripentylphosphite, triphenylphosphite, tripropylphosphite, tritolylphosphite, trixylylphosphite, or combinations thereof.

In an embodiment, the organophosphorus compound can comprise phosphinites, which can be represented by the general formula of $(R)_2(OR')_1P$; wherein each R can be hydrogen, a hydrocarbyl group, or combinations thereof and wherein each R' can be a hydrocarbyl group. Examples of phosphinites suitable for use as phosphate precursors in this disclosure include without limitation (1-methylethyl)diphenylphosphinite, 2-ethylphenyldiphenyl phosphinite, 4-(diphenylmethyl)phenyl]diphenylphosphinite, bis(2-methylphenyl)(2-methylpropyl) phosphinite, butyldiethylphosphinite, butyldimethylphosphinite, butyldiphenylphosphinite, butyldipropylphosphinite, crecyldiphenylphosphinite, cyclohexyldiphenylphosphinite, decyldiethylphosphinite, decyldimethylphosphinite, decyldiphenylphosphinite, dibutyl(2-methylphenyl) phosphinite, dicyclohexylphenylphosphinite, diethyl(3-methylphenyl)phosphinite, ethyldibutylphosphinite, ethyldimethylphosphinite, ethyldioctylphosphinite, ethyldiphenylphosphinite, ethyldipropylphosphinite, heptyldibutylphosphinite, heptyldiethylphosphinite, heptyldimethyl phosphinite, heptyldipentylphosphinite, heptyldiphenylphosphinite, hexyldibutylphosphinite, hexyldiethylphosphinite, hexyldimethyl phosphinite, hexyldipentylphosphinite, hexyldiphenylphosphinite, methylbis(4-methylphenyl) phosphinite, methyldibutylphosphinite, methyldidecylphosphinite, methyldiethylphosphinite, methyldiphenylphosphinite, methyldipropylphosphinite, octyldimethylphosphinite, octyldiphenylphosphinite, pentyldibutylphosphinite, pentyldiethylphosphinite, pentyldimethylphosphinite, pentyldiphenylphosphinite, phenyldibutylphosphinite, phenyldiethylphosphinite, phenyldimethylphosphinite, phenyldipropylphosphinite, propyldibutylphosphinite, propyldimethylphosphinite, propyldiphenylphosphinite, tri(2-chloroethyl) phosphinite, tri(nonylphenyl) phosphinite, tris(2,3-dichloropropyl) phosphinite, tris(2,6-dimethylphenyl) phosphinite, tris(2-methylphenyl) phosphinite, tris(4-methylphenyl) phosphinite, tris(methoxyphenyl)phosphinite, tris[4-(1,1-dimethylethyl)phenyl] phosphinite, tri-t-butylphosphinite, or combinations thereof. In some embodiments, the phosphinites suitable for use in this disclosure include without limitation tributylphosphinite, tricresyl phosphinite, tricyclohexyl phosphinite, tridecylphosphinite, triethylphosphinite, triheptylphosphinite, triisopropylphosphinite, trimethylphosphinite, trioctadecylphosphinite, trioctylphosphinite, tripentylphosphinite, triphenylphosphinite, tripropylphosphinite, tritolylphosphinite, trixylylphosphinite, or combinations thereof.

In an embodiment, the organophosphorus compound can comprise phosphonites, which can be represented by the general formula of $(R)_1(OR')_2P$; wherein each R can be hydrogen, a hydrocarbyl group, or combinations thereof and wherein each R' can be a hydrocarbyl group. Examples of phosphonites suitable for use as phosphate precursors in this disclosure include without limitation (1-methylethyl)diphenylphosphonite, 2-ethylphenyldiphenyl phosphonite, 4-(diphenylmethyl)phenyl]diphenylphosphonite, bis(2-methylphenyl)(2-methylpropyl) phosphonite, butyldiethylphosphonite, butyldimethylphosphonite, butyldiphenylphosphonite, butyldipropylphosphonite, crecyldiphenylphosphonite, cyclohexyldiphenylphosphonite, decyldiethylphosphonite, decyldimethylphosphonite, decyldiphenylphosphonite, dibutyl(2-methylphenyl) phosphonite, dicyclohexylphenylphosphonite, diethyl(3-methylphenyl)phosphonite, ethyldibutylphosphonite, ethyldimethylphosphonite, ethyldioctylphosphonite, ethyldiphenylphosphonite, ethyldipropylphosphonite, heptyldibutylphosphonite, heptyldiethylphosphonite, heptyldimethyl phosphonite, heptyldipentylphosphonite, heptyldiphenylphosphonite, hexyldibutylphosphonite, hexyldiethylphosphonite, hexyldimethyl phosphonite, hexyldipentylphosphonite, hexyldiphenylphosphonite, methylbis(4-methylphenyl) phosphonite, methyldibutylphosphonite, methyldidecylphosphonite, methyldiethylphosphonite, methyldiphenylphosphonite, methyldipropylphosphonite, octyldimethylphosphonite, octyldiphenylphosphonite, pentyldibutylphosphonite, pentyldiethylphosphonite, pentyldimethylphosphonite, pentyldiphenylphosphonite, phenyldibutylphosphonite, phenyldiethylphosphonite, phenyldimethylphosphonite, phenyldipropylphosphonite, propyldibutylphosphonite, propyldimethylphosphonite, propyldiphenylphosphonite, tri(2-chloroethyl) phosphonite, tri(nonylphenyl) phosphonite, tris(2,3-dichloropropyl) phosphonite, tris(2,6-dimethylphenyl) phosphonite, tris(2-methylphenyl) phosphonite, tris(4-methylphenyl) phosphonite, tris(methoxyphenyl)phosphonite, tris[4-(1,1-dimethylethyl)phenyl] phosphonite, tri-t-butylphosphonite, or combinations thereof. In some embodiments, the phosphonites suitable for use in this disclosure include without limitation tributylphosphonite, tricresyl phosphonite, tricyclohexyl phosphonite, tridecylphosphonite, triethylphosphonite, triheptylphosphonite, triisopropylphosphonite, trimethylphosphonite, trioctadecyl phosphonite, trioctylphosphonite, trip entylpho sphonite, triphenylphosphonite, tripropylphosphonite, tritolylphosphonite, trixylylphosphonite, or combinations thereof.

In an embodiment, the organophosphorus compound, organophosphorus compound precursor, or combinations thereof, can be present in the mixture for the preparation of the hydrogenation catalyst in an amount of from about 0.005 wt. % to about 5 wt. % based on the weight of phosphorus to the total weight of the hydrogenation catalyst; alternatively, from about 0.01 wt. % to about 1 wt. %; alternatively, from about 0.01 wt. % to about 0.5 wt. %. The amount of organophosphorus compound or phosphorus incorporated into the hydrogenation catalyst can be in the range described herein for the amount of organophosphorus compound or organophosphorus precursor used to prepare the hydrogenation catalyst. Additionally or alternatively, the amount of hydrogenation catalyst can have about 300 ppmw phosphorous based on the total weight of the hydrogenation catalyst.

In an embodiment, the hydrogenation catalyst can further comprise one or more selectivity enhancers. Suitable selectivity enhancers include, but are not limited to, Group 1B metals, Group 1B metal compounds, silver compounds, fluorine, fluoride compounds, sulfur, sulfur compounds, alkali metals, alkali metal compounds, alkaline metals, alkaline metal compounds, iodine, iodide compounds, or combinations thereof. In an embodiment, the hydrogenation catalyst can comprise one or more selectivity enhancers which can be present in total in the mixture for preparation of the hydrogenation catalyst in an amount of from about 0.001 to about 10 wt. % based on the total weight of the hydrogenation catalyst; alternatively, from about 0.01 to about 5 wt. %; alternatively, from about 0.01 to about 2 wt. %. The amount of selectivity enhancer incorporated into the hydrogenation catalyst can be in the range described herein for the amount of selectivity enhancer used to prepare the hydrogenation catalyst.

In an embodiment, the selectivity enhancer can comprise silver (Ag), silver compounds, or combinations thereof. Examples of suitable silver compounds include without limitation silver nitrate, silver acetate, silver bromide, silver chloride, silver iodide, silver fluoride, or combinations thereof. In an embodiment, the selectivity enhancer can comprise silver nitrate. The hydrogenation catalyst can be prepared using silver nitrate in an amount of from about 0.005 wt. % to about 5 wt. % silver based on the total weight of the hydrogenation catalyst; alternatively, from about 0.01 wt. % to about 1 wt. % silver; alternatively, from about 0.01 wt. % to about 0.5 wt. %. The amount of silver incorporated into the hydrogenation catalyst can be in the range described herein for the amount of silver nitrate used to prepare the hydrogenation catalyst.

In an embodiment, the selectivity enhancer can comprise alkali metals, alkali metal compounds, or combinations thereof. Examples of suitable alkali metal compounds include without limitation elemental alkali metals, alkali metal halides (for example alkali metal fluoride, alkali metal chloride, alkali metal bromide, alkali metal iodide), alkali metal oxides, alkali metal carbonate, alkali metal sulfate, alkali metal phosphate, alkali metal borate, or combinations thereof. In an embodiment, the selectivity enhancer can comprise potassium fluoride (KF). In another embodiment, the hydrogenation catalyst can be prepared using an alkali metal compound in an amount of from about 0.01 wt. % to about 5 wt. % based on the total weight of the hydrogenation catalyst; alternatively, from about 0.05 wt. % to about 2 wt. %; alternatively, from about 0.05 wt. % to about 1 wt. %. The amount of alkali metal incorporated into the hydrogenation catalyst can be in the range described herein for the amount of alkali metal compound used to prepare the hydrogenation catalyst.

In an embodiment, a method of preparing a hydrogenation catalyst can initiate with the contacting of an inorganic support with a palladium-containing compound to form a supported palladium composition. The contacting can be carried out using any suitable technique. For example, the inorganic support can be contacted with the palladium-containing compound by incipient wetness impregnation of the support with a palladium-containing solution. In such embodiments, the resulting supported palladium composition can have greater than about 90 wt. %; alternatively, from about 92 wt. % to about 98 wt. %; alternatively, from about 94 wt. % to about 96 wt. % of the palladium concentrated near the periphery of the palladium supported composition, as to form a palladium skin.

The palladium skin can be any thickness as long as such thickness can promote the hydrogenation processes disclosed herein. Generally, the thickness of the palladium skin can be in the range of from about 1 micron to about 3000 microns; alternatively, from about 5 microns to about 2000 microns; alternatively, from about 10 microns to about 1000 microns; alternatively, from about 50 microns to about 500 microns. Examples of such methods are further described in more details in U.S. Pat. Nos. 4,404,124 and 4,484,015, each of which is incorporated by reference herein in its entirety.

Any suitable method can be used for determining the concentration of the palladium in the skin of the palladium supported composition or the thickness of the skin. For example, one method involves breaking open a representative sample of the palladium supported composition particles and treating the palladium supported composition particles with a dilute alcoholic solution of N,N-dimethyl-para-nitrosoaniline. The treating solution reacts with the palladium to give a red color that can be used to evaluate the distribution of the palladium. Yet another technique for measuring the concentration of the palladium in the skin of the palladium supported composition involves breaking open a representative sample of catalyst particles, followed by treating the particles with a reducing agent such as hydrogen to change the color of the skin and thereby evaluate the distribution of the palladium. Alternatively, the palladium skin thickness can be determined using the electron microprobe method.

The supported palladium composition formed by contacting the inorganic support with the palladium-containing solution optionally can be dried at a temperature of from about 15° C. to about 150° C.; alternatively, from about 30° C. to about 140° C.; alternatively, from about 60° C. to about 130° C.; and for a period of from about 0.1 hour to about 100 hours; alternatively, from about 2 hours to about 20 hours; alternatively, from about 0.3 hour to about 10 hours. Alternatively, the palladium supported composition can be calcined. This calcining step can be carried out at temperatures up to about 850° C.; alternatively, of from about 150° C. to about 750° C.; alternatively, from about 150° C. to about 700° C.; alternatively, from about 150° C. to about 680° C.; and for a period of from about 0.2 hour to about 20 hours; alternatively, from about 0.5 hour to about 20 hours; alternatively, from about 1 hour to about 10 hours.

In an embodiment, a method of preparing a hydrogenation catalyst further can comprise contacting the supported palladium composition with an organophosphorus compound of the type described herein (for example phosphine oxide, phosphate, an organophosphorus compound precursor such as an phosphate or an phosphine). The contacting can be carried out in any suitable manner that will yield a hydrogenation catalyst meeting the parameters described herein such as for example by incipient wetness impregnation. Briefly, the organophosphorus compound can comprise phosphine oxide which is dissolved in a solvent, such as for example, water, acetone, isopropanol, etc., to form a phosphine oxide containing solution. The phosphine oxide containing solution can be added to the supported palladium composition to form a palladium/phosphine oxide supported composition (herein this particular embodiment of the hydrogenation catalyst is referred to as a Pd/PO composition).

In some embodiments, one or more selectivity enhancers of the type described previously herein can be added to the supported palladium composition prior to or following the contacting of same with an organophosphorus compound. In an embodiment, this addition can occur by soaking the supported palladium composition (with or without the organophosphorus compound) in a liquid comprising one or more suitable selectivity enhancers. In another embodiment, this addition can occur by incipient wetness impregnation of the supported palladium composition (with or without an organophosphorus compound) with liquid comprising one or more suitable selectivity enhancers to form an enhanced supported palladium composition.

In an embodiment, silver can be added to the supported palladium composition (without an organophosphorus compound). For example, the supported palladium composition can be placed in an aqueous silver nitrate solution of a quantity greater than that necessary to fill the pore volume of the composition. The resulting material is a palladium/silver supported composition (herein this particular embodiment of the hydrogenation catalyst is referred to as a Pd/Ag composition). In an embodiment, the Pd/Ag composition is further contacted with an organophosphorus compound. The contacting can be carried out as described above to form a palladium/silver/phosphine oxide composition. In another embodiment, the Pd/Ag composition is further contacted with a phosphine oxide compound (herein this particular embodiment of the hydrogenation catalyst is referred to as a Pd/Ag/PO composition).

In an embodiment, one or more alkali metals can be added to the Pd/Ag composition (prior to or following contacting with an organophosphorus compound) using any suitable technique such as those described previously herein. In an embodiment, the selectivity enhancer can comprise potassium fluoride, and the resulting material is a palladium/silver/alkali metal fluoride supported composition (herein this particular embodiment of the hydrogenation catalyst is referred to as a Pd/Ag/KF composition).

In an embodiment, the supported palladium composition is contacted with both an alkali metal halide and a silver compound (prior to or following contacting with an organophosphorus compound). Contacting of the supported palladium composition with both an alkali metal halide and a silver compound can be carried out simultaneously; alternatively the contacting can be carried out sequentially in any user-desired order.

In an embodiment, one or more selectivity enhancers are contacted with the supported palladium composition prior to contacting the composition with an organophosphorus compound. In such embodiments, the resulting composition comprising Pd/Ag, Pd/KF, or Pd/Ag/KF can be calcined under the conditions described previously herein, and subsequently contacted with an organophosphorus compound. For example, a phosphine oxide (PO) can be added to the Pd/Ag, Pd/KF, or Pd/Ag/KF composition to provide Pd/Ag/PO, Pd/KF/PO, or Pd/Ag/KF/PO composition. In an alternative embodiment, one or more selectivity enhancers are contacted with the supported palladium composition following contacting of the composition with an organophosphorus compound. For example, Ag, KF, or combinations thereof can be added to the Pd/PO composition to provide Pd/Ag/PO, Pd/KF/PO, or Pd/Ag/KF/PO compositions. In yet another alternative embodiment, one or more selectivity enhancers can be contacted with the palladium supported composition and an organophosphorus compound simultaneously.

In an embodiment, a hydrogenation catalyst formed in accordance with the methods disclosed herein can comprise an α-alumina support, palladium, and an organophosphorus compound. In an alternative embodiment, a hydrogenation catalyst formed in accordance with the methods disclosed herein can comprise an α-alumina support, palladium, an organophosphorus compound (for example phosphine oxide) and one or more selectivity enhancers, (for example silver, potassium fluoride, or combinations thereof). The hydrogenation catalyst (Pd/PO, Pd/Ag/PO, Pd/KF/PO, or the Pd/Ag/KF/PO compositions) can be dried to form a dried hydrogenation catalyst. In some embodiments, this drying step can be carried out at a temperature in the range of from about 0° C. to about 150° C.; alternatively, from about 30° C. to about 100° C.; alternatively, from about 50° C. to about 80° C.; and for a period of from about 0.1 hour to about 100 hours; alternatively, from about 0.5 hour to about 20 hours; alternatively, from about 1 hour to about 10 hours. In an embodiment, the organophosphorus compound can comprise an organophosphorus compound precursor which upon exposure to air, the temperature ranges used during drying of the aforementioned composition or both is converted to an organophosphorus compound of the type described herein.

The dried hydrogenation catalyst can be reduced using hydrogen gas or a hydrogen gas containing hydrocarbon, for example the hydrocarbon stream of the process, thereby providing for optimum operation of the process. Such a gaseous hydrogen reduction can be carried out at a temperature in the range of from, for example, about 0° C. to about 150° C.; alternatively, 10° C. to about 100° C.; alternatively, about 20° C. to about 80° C. Additionally or alternatively, the dried hydrogenation catalyst can be reduced in a pressurized atmosphere and at a disclosed temperature, such as ambient temperature for a period of about 8 to about 24 hours.

In an embodiment, a method of preparing a hydrogenation catalyst can comprise contacting an inorganic support with a palladium-containing compound (for example palladium chloride, or palladium nitrate) to form a palladium supported composition; drying and calcining the palladium supported composition to form a dried and calcined palladium supported composition. The dried and calcined palladium supported composition can then be contacted with a silver-containing compound (for example silver nitrite, or silver fluoride) to form a Pd/Ag composition which can then be dried and/or calcined to form a dried and/or calcined Pd/Ag composition. The dried and/or calcined Pd/Ag composition can be contacted with an alkali metal fluoride (for example potassium fluoride) to form a Pd/Ag/KF composition which is then dried and calcined. The dried and calcined Pd/Ag/KF composition can then be contacted with an organophosphorus compound (for example phosphine oxide or a precursor) to form a hydrogenation catalyst. In an alternative embodiment, the Pd/Ag/KF composition can be added to an unsaturated hydrocarbon and the organophosphorus compound can be separately added to the unsaturated hydrocarbon so that the Pd/Ag/KF composition contacts the organophosphorus compound to form the hydrogenation catalyst while in contact with the unsaturated hydrocarbon. The hydrogenation catalyst can be further processed by drying the hydrogenation catalyst to form a dried hydrogenation catalyst. The contacting, drying, and calcining can be carried out using any suitable technique and conditions such as those described previously herein.

Examples of suitable hydrogenation catalysts and methods for preparation thereof are disclosed U.S. Pat. No. 8,6333,127, U.S. Pat. No. 5,489,565, U.S. Pat. No. 5,585,318, and U.S. Pat. No. 5,510,550, each of which is incorporated herein by reference in its entirety for all purposes.

Embodiments of a hydrogenation process can include cracking a feed stream to produce a cracked gas stream comprising methylacetylene, propadiene, acetylene, ethylene, propylene, ethane, propane, methane, hydrogen, carbon monoxide, $C_4^+$ components, or combinations thereof; fractionating the cracked gas stream into a $C_2^-$ stream and a $C_3^+$ stream, wherein the $C_2^-$ stream can comprise acetylene, ethylene, ethane, carbon monoxide, methane, hydrogen, carbon monoxide, or combinations thereof, and wherein the $C_3^+$ stream can comprise the $C_3^+$ components; hydrogenating at least a portion of the acetylene of the $C_2^-$ stream in the presence of a hydrogenation catalyst to yield a product comprising ethylene, wherein the hydrogenation catalyst has a selectivity for conversion of acetylene to ethylene of about 90 mol % or greater based on the moles of acetylene converted to the product, wherein the hydrogenating occurs in a reaction zone under conditions comprising a flow index ($I_F$) in a range of from about 0.09 to about 35; alternatively, from about 0.27 to about 25; alternatively, from about 0.4 to about 20; alternatively, from about 1.0 to about 5.6, wherein the $I_F$ is defined as:

$$I_F = \frac{F \times [CO]}{V},$$

wherein F is the flow rate of the $C_2^-$ stream into the reaction zone in units of kg/h, [CO] is the concentration of carbon monoxide in the $C_2^-$ stream in units of mol %, and V is the volume of the portion of the reaction zone in units of ft$^3$; removing ethylene from the product; and polymerizing ethylene into one or more polymer products.

Embodiments of a hydrogenation process can also include cracking a feed stream to produce a cracked gas stream comprising methylacetylene, propadiene, acetylene, propylene, ethylene, propane, ethane, methane, hydrogen, carbon monoxide, $C_4^+$ components ($C_4^+$ components comprising $C_4$ hydrocarbons and heavier), or combinations thereof; fractionating the cracked gas stream into a $C_3^-$ stream and a $C_4^+$ stream, wherein the $C_3^-$ stream can comprise methylacetylene, propadiene, acetylene, propylene, ethylene, propane, ethane, carbon monoxide, methane, hydrogen, or combinations thereof, and wherein the $C_4^+$ stream can comprise the $C_4^+$ components; hydrogenating at least a portion of the methylacetylene, propadiene, acetylene, or a combination thereof of the $C_3^-$ stream in the presence of a hydrogenation catalyst to yield a product comprising propylene, ethylene, or both, wherein the hydrogenation catalyst has a selectivity for conversion of methylacetylene, propadiene, acetylene, or a combination thereof to propylene, ethylene, or both of about 90 mol % or greater based on the moles of methylacetylene, propadiene, acetylene, or a combination thereof converted to the product, wherein the hydrogenating step occurs in a reaction zone under conditions comprising a flow index ($I_F$) in a range of from about 0.09 to about 35; alternatively, from about 0.27 to about 25; alternatively, from about 0.4 to about 20; alternatively, from about 1.0 to about 5.6, wherein the $I_F$ is defined as:

$$I_F = \frac{F \times [CO]}{V},$$

wherein F is the flow rate of the $C_3^-$ stream into the reaction zone in units of kg/h, [CO] is the concentration of carbon monoxide in the $C_3^-$ stream in units of mol %, and V is the volume of the portion of the reaction zone in units of ft$^3$; removing propylene, ethylene, or both from the product; and polymerizing propylene, ethylene, or both into one or more polymer products.

In embodiments of the hydrogenation process, the [CO] in the reaction zone ranges from about 0.0001 mol % to about 0.15 mol %.

In embodiments of the hydrogenation process, the highly unsaturated hydrocarbon can comprise acetylene, wherein the unsaturated hydrocarbon can comprise ethylene. In additional or alternative embodiments of the hydrogenation process, the highly unsaturated hydrocarbon can comprise methylacetylene, propadiene, or both; and the unsaturated hydrocarbon can comprise propylene.

In embodiments of the hydrogenation process, the reaction zone 30 can comprise a first stage 31 and a second stage 35, wherein the first stage 31 and the second stage 35 of the reaction zone 30 can comprise the hydrogenation catalyst. The first stage 31 of the reaction zone 30 and the second stage 35 of the reaction zone 30 can be contained in a common vessel; or the first stage 31 of the reaction zone 30 can comprise a first reactor (or the first stage) and the second stage 35 of the reaction zone 30 can comprise a second reactor (or the second stage), wherein the first reactor (or the first stage) and the second reactor (or the second stage) are connected in series.

The hydrogenation catalyst of the hydrogenation process can comprise an embodiment of the catalyst described herein. For example, the hydrogenation catalyst can comprise palladium, an inorganic support, and optionally, an organophosphorus compound. The hydrogenation catalyst can further comprise Group 1B metals, Group 1B metal compounds, silver compounds, fluorine, fluoride compounds, sulfur, sulfur compounds, alkali metals, alkali metal compounds, alkaline earth metals, alkaline earth metal compounds, iodine, iodide compounds, or combinations thereof. The inorganic support has a surface area of from about 2 m$^2$/g to about 100 m$^2$/g, and greater than about 90 wt. % of the palladium is concentrated near a periphery of the support. The organophosphorus compound of the hydrogenation catalyst can be: i) present in an amount of from about 0.005 wt. % to about 5 wt. % based on the total weight of the hydrogenation catalyst; ii) represented by the general formula $(R)_x(OR')_yP=O$, wherein x and y are integers ranging from 0 to 3 and x plus y equals 3, wherein each R is hydrogen, a hydrocarbyl group, or combinations thereof and wherein each R' is a hydrocarbyl group; iii) a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group; iv) a phosphine oxide, a phosphate, a phosphinate, a phosphonate, a phosphine, a phosphite, a phosphinite, a phosphonite, or combinations thereof; or v) combinations thereof.

Additionally or alternatively, embodiments of the disclosed hydrogenation process can also be described using FIG. 1. The hydrogenation process can include feeding or flowing a feed via a feed stream 12 to a furnace 10; thermally cracking the feed stream in the furnace 10 to yield a cracked gas stream 14 comprising compounds including highly unsaturated hydrocarbon, saturated hydrocarbon, carbon monoxide, or combinations thereof; flowing the cracked gas stream 14 from the furnace 10 to a fractionation zone 20 (for example a fractionation zone comprising a demethanizer, a deethanizer, a depropanizer, or combinations thereof), wherein the fractionation zone 20 separates the cracked gas stream 14 into a hydrocarbon stream 24 (for example a hydrocarbon stream comprising an overhead product $C_2^-$ stream for a frontend deethanizer, comprising an overhead product $C_3^-$ stream for a frontend depropanizer, or comprising a bottoms product $C_2^+$ stream for a frontend demethanizer) and a stream 22 (for example a stream comprising a bottoms product $C_3^+$ stream for a frontend deethanizer, comprising a bottoms product $C_4^+$ stream for a frontend depropanizer, or comprising an overhead methane-rich stream for a frontend demethanizer); providing (via hydrocarbon stream 24) a highly unsaturated hydrocarbon and carbon monoxide to reaction zone 30 comprising a hydrogenation catalyst; and hydrogenating the highly unsaturated hydrocarbon to yield a product comprising an unsaturated hydrocarbon in the reaction zone 30, wherein the hydrogenation catalyst has a selectivity for conversion of the highly unsaturated hydrocarbon to the unsaturated hydrocarbon of about 90 mol % or greater based on the moles of the highly unsaturated hydrocarbon which were converted to the product, and wherein the hydrogenating step occurs under conditions comprising a flow index ($I_F$) in a range of from about 0.09 to about 35; alternatively, from about 0.27 to about 25; alternatively, from about 0.4 to about 20; alternatively, from about 1.0 to about 5.6, wherein the $I_F$ is defined as:

$$I_F = \frac{F \times [CO]}{V},$$

wherein F is flow rate of the hydrocarbon stream 24 into the reaction zone 30 in units of kg/h, [CO] is the concentration of carbon monoxide in the hydrocarbon stream 24 in units of mol %, and V is the volume of the portion of the reaction zone 30 in units of ft$^3$. In embodiments of the hydrogenation process, the reaction zone 30 can comprise a single stage reaction zone or a multi-stage reaction zone (for example a reaction zone comprising a first stage 31 and a second stage 35). Hydrogenation in the reaction zone 30 can comprise contacting the hydrogenation catalyst with the highly unsaturated hydrocarbon in the presence of hydrogen (for example hydrogen can be included in the hydrocarbon stream 24 or a separate supply of hydrogen can feed to the reaction zone 30 by techniques disclosed herein or known in the art with the aid of this disclosure); or combinations thereof. Contacting the hydrogenation catalyst with the highly unsaturated hydrocarbon in the presence of hydrogen can be conducted at a temperature less than about the boiling point of a component of the hydrogenation catalyst (for example an organophosphorus compound).

Various benefits and advantages can be achieved with the disclosed embodiments.

For example, the hydrogenation catalysts disclosed herein can be used for the hydrogenation of a highly unsaturated hydrocarbon at high conversions in a reaction zone without sacrificing catalyst selectivity (for example selectivity for conversion of the highly unsaturated hydrocarbon to the unsaturated hydrocarbon can be greater than about 90 mol % for all conversion embodiments). As such, the disclosed embodiments allow near 100 mol % conversion of a highly unsaturated hydrocarbon from the hydrocarbon stream 24 in disclosed embodiments.

Moreover, embodiments of the disclosed system and process can operate at low carbon monoxide levels (for example less than about 100 ppmv, 20 to 50 ppmv) without introducing further risk of reaction instability or runaway reaction conditions.

Additionally, embodiments of the disclosed system and process can withstand fluctuations in the carbon monoxide concentration, for example, if [CO] is lower than 100 ppmv at one point in time and higher at another point in time due to high amounts of carbon monoxide, for example, in a feed stream 12 comprising a high [CO] FCC gas.

Further, it is believed that the risk of runaway reactions is low when embodiments of the disclosed system and process operate at conditions within the flow index ($I_F$) range disclosed herein.

Moreover still, embodiments having or using a front-end deethanizer configuration can be used in processes and systems having a process stream comprising large amounts of saturated hydrocarbon (for example cracked gas stream 14). In such processes and systems, alkynes heavier than acetylene may not feed to the first stage 31 of the reaction zone 30, and as such, first stage 31 of the reaction zone 30 operate at high conversions without the risk of runaway reactions associated with streams of other compositions.

Additionally, the hydrogenation catalyst comprising an embodiment of the organophosphorus compound can display an increased activity over some time period and enhanced initial selectivity wherein the organophosphorus compound is associated with the hydrogenation catalyst. This can be advantageous for reactions employing a fresh catalyst as the organophosphorus compound can allow for a more stable operation and a reduction in the potential for a runaway reaction due to the increase in catalyst selectivity and predictable catalytic activity as the composition stabilizes.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

In the following examples, the performance of a hydrogenation catalyst were compared at two flow indexes. A catalyst sample was prepared on α-Al$_2$O$_3$ pellets supplied by Süd Chemie, Heufeld, Germany in the form of 4 mm×4 mm tablets as described in U.S. Pat. Nos. 5,489,565; 5,585,318; and 5,587,348, each of which is incorporated by reference herein in its entirety. The α-Al$_2$O$_3$ pellets had a surface area of about 5 to about 7 m$^2$/g (determined by the BET method employing N$_2$).

The catalyst was evaluated by placing a 20 ml (7.06E-04 ft$^3$) catalyst sample inside a jacketed stainless steel reactor with an inside diameter of about 0.67 inches and a length of about 18 inches. The catalyst resided in the middle of the reactor; both ends of the reactor were packed with 14 grit alundum; and a 0.19 inch diameter thermowell was centered in the catalyst bed. The reactor temperature was controlled by circulating a heating medium containing a mixture of ethylene glycol and water through the jacket of the reactor. The catalyst was first reduced at a catalyst bed temperature of about 100° F. (about 37.8° C.) to 200° F. (about 93.3° C.) for about 1 hour under hydrogen gas flowing at 200 ml/min at 200 pounds per square inch gauge (psig). The catalyst bed was then cooled to a temperature below the anticipated T1 temperature. If the T1 temperature was not known, the catalyst bed was cooled to a temperature about 75° F. (about 23.9° C.) to about 85° F. (about 29.4° C.). Thereafter, a hydrocarbon stream was continuously introduced to the reactor at a flow rate of 900 ml/min (0.040 kg/hr) at 200 psig. The composition of the hydrocarbon stream was prepared by adding the stated amounts of carbon monoxide catalyst to a hydrocarbon stream having the composition of Table 2. The hydrocarbon stream composition of Table 2 is typical of a hydrocarbon feed from the top of a deethanizer fractionation tower in an ethylene plant.

TABLE 2

| Reactor Feed Component | mol % |
|---|---|
| Hydrogen | 26.63 |
| Methane | 25.81 |
| Acetylene | 0.16 |
| Ethylene | 47.36 |

While the hydrocarbon stream was passing over the catalyst the effluent was regularly sampled and analyzed by gas chromatography. The catalyst bed temperature was determined by inserting a thermocouple into the thermowell and varying its position to determine the highest temperature for the catalyst bed. Then the reactor jacket temperature was raised a few degrees, and the testing cycle was repeated until the acetylene concentration in the effluent dropped below 20 ppm. The testing cycle continued until 3 weight % of ethane was measured in the effluent. The cleanup temperature, T1, is defined as the temperature at which the acetylene concentration drops below 20 ppm. The T2, or runaway temperature, is defined as the temperature at which 3 wt % of ethane is produced. At this temperature, the uncontrolled hydrogenation of ethylene to ethane may occur. The delta T (ΔT) is the difference between T2 and T1. This value can be viewed as a measure of the selectivity of the hydrogenation catalyst or even a window of operability.

TABLE 3

| Test | [CO] (mol %) | Flow Index ($I_F$) [(kg mol %)/ (hr ft$^3$)] | T1 (° F.) | T2 (° F.) | ΔT (° F.) | Notes |
|---|---|---|---|---|---|---|
| 1 | 0.034 | 1.912 | 112 | 176 | 64 | Normal Operations |
| 2 | 0.0005 | 0.028 | * | * | * | * Run Away prior to reaching T1 |

The temperature T1 in Test 1 of 112° F. is about 44.4° C. The temperature T2 in Test 1 of 176° F. is about 80.0° C. The temperature ΔT in Test 1 of 64° F. is about 17.8° C.

During the selective hydrogenation experiment with a Flow index of 1.912 the process performed consistently and predictably with a good window of operations as determined by the ΔT. However, under Test 2 at a flow index at 0.028, the hydrogenation process was not controllable and a T1 was not measurable. At these conditions, the hydrogenation reaction ran away at little more than room temperature.

ADDITIONAL DESCRIPTION

Embodiments of a system and process have been described. The following are a first set of nonlimiting, specific embodiments in accordance with the present disclosure:

A first embodiment, which is a process comprising:
hydrogenating, in a reaction zone, a highly unsaturated hydrocarbon received from a hydrocarbon stream to yield a product comprising an unsaturated hydrocarbon, wherein the hydrogenating step occurs in the presence of a hydrogenation catalyst which has a selectivity for conversion of the highly unsaturated hydrocarbon to the unsaturated hydrocarbon of about 90 mol % or greater based on the moles of the highly unsaturated hydrocarbon which are converted to the product,
wherein the hydrogenating step occurs in a reaction zone under conditions comprising a flow index ($I_F$) in a range of about 0.09 to about 35, wherein the $I_F$ is defined as:

$$I_F = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the reaction zone in units of ft$^3$.

A second embodiment, which is the process of the first embodiment, wherein the selectivity is defined as:

$$S = 100 \times \left( \frac{UH(p) - UH(f)}{HUH(f) - HUH(p)} \right)$$

where S is selectivity in mol %, UH(p) is moles of the unsaturated hydrocarbon in the product, UH(f) is moles of the unsaturated hydrocarbon in the hydrocarbon stream, HUH(f) is the moles of highly unsaturated hydrocarbon in the hydrocarbon stream, and HUH(p) is the moles of the highly unsaturated hydrocarbon in the product.

A third embodiment, which is the process of any of the first through the second embodiments, wherein the highly unsaturated hydrocarbon comprises acetylene, and wherein the unsaturated hydrocarbon comprises ethylene.

A fourth embodiment, which is the process of any of the first through the third embodiments, wherein the highly unsaturated hydrocarbon comprises methylacetylene, propadiene, or both; and wherein the unsaturated hydrocarbon comprises propylene.

A fifth embodiment, which is the process of any of the first through the fourth embodiments, further comprising:
cracking a feed stream to produce a cracked gas stream comprising the highly unsaturated hydrocarbon, carbon monoxide, and a saturated hydrocarbon.

A sixth embodiment, which is the process of the fifth embodiment, further comprising:
fractionating the cracked gas stream to yield a $C_3^-$ stream or a $C_2^-$ stream comprising the highly unsaturated hydrocarbon, carbon monoxide, and about 90 mol % or greater of the saturated hydrocarbon contained in the cracked gas stream, wherein at least a portion of the highly unsaturated hydrocarbon in the $C_3^-$ stream or the $C_2^-$ stream is hydrogenated in the presence of the hydrogenation catalyst.

A seventh embodiment, which is the process of any of the first through the sixth embodiments, wherein the [CO] in the reaction zone is from about 0.0001 mol % to about 0.15 mol %.

An eighth embodiment, which is the process of any of the first through the seventh embodiments, wherein the hydrogenating step comprises:
contacting the hydrogenation catalyst with at least a portion of the highly unsaturated hydrocarbon in the presence of hydrogen.

A ninth embodiment, which is the process of any of the first through the eighth embodiments, wherein the reaction zone comprises a first stage and a second stage, wherein at least one of the first stage and the second stage of the reaction zone contains the hydrogenation catalyst.

A tenth embodiment, which is the process of the ninth embodiment, wherein:
i) the first stage of the reaction zone and the second stage of the reaction zone are contained in a common vessel; or
ii) the first stage of the reaction zone is a first reactor, the second stage of the reaction zone is a second reactor, and the first reactor and the second reactor are connected in series.

An eleventh embodiment, which is the process of any of the first through the tenth embodiments, wherein the hydrogenation catalyst comprises palladium, an inorganic support, and optionally, an organophosphorus compound.

A twelfth embodiment, which is the process of the eleventh embodiment, wherein the hydrogenation catalyst further comprises Group 1B metals, Group 1B metal compounds, silver compounds, fluorine, fluoride compounds, sulfur, sulfur compounds, alkali metals, alkali metal compounds, alkaline earth metals, alkaline earth metal compounds, iodine, iodide compounds, or combinations thereof.

A thirteenth embodiment, which is the process of any of the eleventh through the twelfth embodiments, wherein the inorganic support has a surface area of from about 2 m$^2$/g to about 100 m²/g, and greater than about 90 wt. % of the palladium is concentrated near a periphery of the of the inorganic support.

A fourteenth embodiment, which is the process of any of the eleventh through the thirteenth embodiments, wherein the organophosphorus compound of the hydrogenation catalyst is:

i) present in an amount of from about 0.005 wt. % to about 5 wt. % based on the total weight of the hydrogenation catalyst;

ii) represented by a general formula $(R)_x(OR')_yP=O$, wherein x and y are integers ranging from 0 to 3 and x plus y equals 3, wherein each R is hydrogen, a hydrocarbyl group, or combinations thereof; and wherein each R' is a hydrocarbyl group;

iii) a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group;

iv) a phosphine oxide, a phosphate, a phosphinate, a phosphonate, a phosphine, a phosphite, a phosphinite, a phosphonite, or combinations thereof; or v) combinations thereof.

A fifteenth embodiment, which is a system comprising:

a hydrocarbon stream comprising a highly unsaturated hydrocarbon and carbon monoxide; and a reaction zone receiving the hydrocarbon stream, wherein the reaction zone contains at least one hydrogenation catalyst, wherein the highly unsaturated hydrocarbon is hydrogenated in the reaction zone to yield a product comprising an unsaturated hydrocarbon, wherein the at least one hydrogenation catalyst has a selectivity for conversion of the highly unsaturated hydrocarbon to the unsaturated hydrocarbon of about 90 mol % or greater based on the moles of the highly unsaturated hydrocarbon which are converted to the product, wherein the reaction zone comprises a flow index ($I_F$) in a range of about 0.09 to about 35, wherein the $I_F$ is defined as:

$$I_F = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the portion of the reaction zone in units of ft³.

A sixteenth embodiment, which is the system of the fifteenth embodiment, wherein the selectivity is defined as:

$$S = 100 \times \left(\frac{UH(p) - UH(f)}{HUH(f) - HUH(p)}\right)$$

where S is the selectivity in mol %, UH(p) is moles of the unsaturated hydrocarbon in the product, UH(f) is moles of the unsaturated hydrocarbon in the hydrocarbon stream, HUH(f) is the moles of highly unsaturated hydrocarbon in the hydrocarbon stream, and HUH(p) is the moles of the highly unsaturated hydrocarbon in the product.

A seventeenth embodiment, which is the system of any of the fifteenth through the sixteenth embodiments, further comprising:

a tube in a furnace fluidly connected to and upstream of the reaction zone, wherein at least a portion of the tube is made of a co-production metal; and a cracked gas stream comprising the highly unsaturated hydrocarbon, a saturated hydrocarbon, and carbon monoxide flowing from the tube.

An eighteenth embodiment, which is the system of the seventeenth embodiment, further comprising:

a fractionation zone comprising a deethanizer or a depropanizer fluidly connected to and upstream of the reaction zone, wherein the fractionation zone fractionates the cracked gas stream into an overhead product and a bottoms product, wherein the overhead product comprises the highly unsaturated hydrocarbon, carbon monoxide, and about 90 mol % or greater of the saturated hydrocarbon contained in the cracked gas stream, wherein the overhead product flows to the reaction zone from the fractionation zone via the hydrocarbon stream.

A nineteenth embodiment, which is the system of any of the seventeenth through the eighteenth embodiments, further comprising:

wherein the co-production metal comprises chromed steel, aluminized steel, or both.

A twentieth embodiment, which is the system of the nineteenth embodiment, wherein:

i) the chromed steel is a steel coated with chromium;

ii) the aluminized steel is a steel coated with aluminum;

iii) the chromed steel is an alloy comprising chromium and a steel;

iv) the aluminized steel is an alloy comprising aluminum and a steel; or v) combinations thereof.

A twenty-first embodiment, which is the system of any of the fifteenth through the twentieth embodiments, wherein the [CO] in the reaction zone is from about 0.0001 mol % to about 0.15 mol %.

A twenty-second embodiment, which is the system of any of the fifteenth through the twenty-first embodiments, wherein the reaction zone comprises a first stage and a second stage, wherein the first stage, the second stage, or both contains the at least one hydrogenation catalyst.

A twenty-third embodiment, which is the system of the twenty-second embodiment, wherein:

i) the first stage of the reaction zone is a first reactor, wherein the second stage of the reaction zone is a second reactor; or ii) the first stage of the reaction zone and the second stage of the reaction zone are contained in a common vessel.

A twenty-fourth embodiment, which is the system of any of the fifteenth through the twenty-third embodiments, wherein the highly unsaturated hydrocarbon comprises acetylene, wherein the unsaturated hydrocarbon comprises ethylene.

A twenty-fifth embodiment, which is the system of any of the fifteenth through the twenty-fourth embodiments, wherein the highly unsaturated hydrocarbon comprises methylacetylene, propadiene, or both; and wherein the unsaturated hydrocarbon comprises propylene.

A twenty-sixth embodiment, which is the system of any of the fifteenth through the twenty-fifth embodiments, wherein the hydrogenation catalyst comprises palladium, an inorganic support, and optionally, an organophosphorus compound.

A twenty-seventh embodiment, which is the system of the twenty-sixth embodiment, wherein the hydrogenation catalyst further comprises Group 1B metals, Group 1B metal compounds, silver compounds, fluorine, fluoride compounds, sulfur, sulfur compounds, alkali metals, alkali metal compounds, alkaline earth metals, alkaline earth metal compounds, iodine, iodide compounds, or combinations thereof.

A twenty-eighth embodiment, which is the system of any of the twenty-sixth through the twenty-seventh embodiments, wherein the inorganic support has a surface area of from about 2 m²/g to about 100 m²/g, and greater than about 90 wt. % of the palladium is concentrated near a periphery of the inorganic support.

A twenty-ninth embodiment, which is the system of any of the twenty-sixth through the twenty-eighth embodiments, wherein the organophosphorus compound of the hydrogenation catalyst is:

i) present in an amount of from about 0.005 wt. % to about 5 wt. % based on the total weight of the hydrogenation catalyst;

ii) represented by a general formula $(R)_x(OR')_yP=O$, wherein x and y are integers ranging from 0 to 3 and x plus y equals 3, wherein each R is hydrogen, a hydrocarbyl group, or combinations thereof and wherein each R' is a hydrocarbyl group;

iii) a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof and wherein each R' is a hydrocarbyl group;

iv) a phosphine oxide, a phosphate, a phosphinate, a phosphonate, a phosphine, a phosphite, a phosphinite, a phosphonite, or combinations thereof or v) combinations thereof.

A thirtieth embodiment, which is a system comprising:

a furnace comprising at least one tube comprising a co-production metal;

a cracked gas stream comprising a highly unsaturated hydrocarbon, a saturated hydrocarbon, and carbon monoxide flowing from the at least one tube;

a fractionation zone comprising a deethanizer or a depropanizer, wherein the fractionation zone fractionates the cracked gas stream into an overhead product and a bottoms product, wherein the overhead product comprises the highly unsaturated hydrocarbon, carbon monoxide, and about 90 mol % or greater of the saturated hydrocarbon contained in the cracked gas stream;

a hydrocarbon stream comprising the overhead product flowing from the fractionation zone; and a reaction zone receiving the hydrocarbon stream, wherein the reaction zone comprises at least one hydrogenation catalyst, wherein, in the reaction zone, the highly unsaturated hydrocarbon is hydrogenated to yield a product comprising an unsaturated hydrocarbon in the reaction zone, wherein the reaction zone comprises a flow index ($I_F$) in a range of about 0.09 to about 35, wherein the $I_F$ is defined as:

$$I_F = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the portion of the reaction zone in units of ft³.

A thirty-first embodiment, which is the system of the thirtieth embodiment, wherein the co-production metal comprises chromed steel, aluminized steel, or both.

A thirty-second embodiment, which is the system of the thirty-first embodiment, wherein:

i) the chromed steel is a steel coated with chromium;

ii) the aluminized steel is a steel coated with aluminum;

iii) the chromed steel is an alloy comprising chromium and a steel;

iv) the aluminized steel is an alloy comprising aluminum and a steel; or v) combinations thereof.

A thirty-third embodiment, which is the system of any of the thirtieth through the thirty-second embodiments, wherein the at least one hydrogenation catalyst has a selectivity for conversion of the highly unsaturated hydrocarbon to the unsaturated hydrocarbon of about 90 mol % or greater based on the moles of the highly unsaturated hydrocarbon which are converted to the product, wherein the selectivity is defined as:

$$S = 100 \times \left( \frac{UH(p) - UH(f)}{HUH(f) - HUH(p)} \right)$$

where S is the selectivity in mol %, UH(p) is moles of the unsaturated hydrocarbon in the product, UH(f) is moles of the unsaturated hydrocarbon in the hydrocarbon stream, HUH(f) is the moles of highly unsaturated hydrocarbon in the hydrocarbon stream, and HUH(p) is the moles of the highly unsaturated hydrocarbon in the product.

A thirty-fourth embodiment, which is the system of the thirty-third embodiment, wherein the at least one hydrogenation catalyst comprises palladium, an inorganic support, and optionally, an organophosphorus compound.

A thirty-fifth embodiment, which is the system of the thirty-fourth embodiment, wherein the organophosphorus compound of the hydrogenation catalyst is:

i) present in an amount of from about 0.005 wt. % to about 5 wt. % based on the total weight of the hydrogenation catalyst;

ii) represented by a general formula $(R)_x(OR')_yP=O$, wherein x and y are integers ranging from 0 to 3 and x plus y equals 3, wherein each R is hydrogen, a hydrocarbyl group, or combinations thereof; and wherein each R' is a hydrocarbyl group;

iii) a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group;

iv) a phosphine oxide, a phosphate, a phosphinate, a phosphonate, a phosphine, a phosphite, a phosphinite, a phosphonite, or combinations thereof; or v) combinations thereof.

A thirty-sixth embodiment, which is the system of any of the thirtieth through the thirty-fifth embodiments, wherein the [CO] in the reaction zone is from about 0.0001 mol % to about 0.15 mol %.

A thirty-seventh embodiment, which is a process comprising:

cracking a feed stream to produce a cracked gas stream comprising acetylene, ethylene, ethane, methane, hydrogen, carbon monoxide, and $C_3^+$ components;

fractionating the cracked gas stream into a $C_2^-$ stream and a $C_3^+$ stream, wherein the $C_2^-$ stream comprises acetylene, ethylene, ethane, methane, carbon monoxide, and hydrogen, wherein the $C_3^+$ stream comprises the $C_3^+$ components;

hydrogenating at least a portion of the acetylene of the $C_2^-$ stream in the presence of a hydrogenation catalyst to yield a product comprising ethylene, wherein the hydrogenation catalyst has a selectivity for conversion of acetylene to ethylene of about 90 mol % or greater based on the moles of acetylene which are converted to the product, wherein the hydrogenating step occurs in a reaction zone under conditions comprising a flow index ($I_F$) in a range of about 0.09 to about 35, wherein the $I_F$ is defined as:

$$I_F = \frac{F \times [CO]}{V},$$

wherein F is the flow rate of the $C_2^-$ stream into the reaction zone in units of kg/h, [CO] is the concentration of carbon monoxide in the $C_2^-$ stream in units of mol %, and V is the volume of the portion of the reaction zone in units of $ft^3$;
  removing ethylene from the product; and
  polymerizing ethylene into one or more polymer products.

A thirty-eighth embodiment, which is the process of the thirty-seventh embodiment, wherein the selectivity is defined as:

$$S = 100 \times \left( \frac{UH(p) - UH(f)}{HUH(f) - HUH(p)} \right)$$

where S is the selectivity in mol %, UH(p) is moles of ethylene in the product, UH(f) is moles of ethylene in the hydrocarbon stream, HUH(f) is the moles of acetylene in the hydrocarbon stream, and HUH(p) is the moles of acetylene in the product.

A thirty-ninth embodiment, which is a process comprising:
  providing a hydrocarbon stream comprising a highly unsaturated hydrocarbon and carbon monoxide to a reaction zone comprising a hydrogenation catalyst; and
  hydrogenating, in the reaction zone, the highly unsaturated hydrocarbon to yield a product comprising an unsaturated hydrocarbon, wherein the hydrogenation catalyst has a selectivity for conversion of the highly unsaturated hydrocarbon to the unsaturated hydrocarbon of about 90 mol % or greater based on moles of the highly unsaturated hydrocarbon which are converted to the product, wherein the hydrogenating step occurs under conditions comprising a flow index ($I_F$) in a range of about 0.09 to about 35, wherein the $I_F$ is defined as:

$$I_f = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the portion of the reaction zone in units of $ft^3$.

A fortieth embodiment, which is the process of the thirty-ninth embodiment, wherein the selectivity is defined as:

$$S = 100 \times \left( \frac{UH(p) - UH(f)}{HUH(f) - HUH(p)} \right)$$

where S is the selectivity in mol %, UH(p) is moles of the unsaturated hydrocarbon in the product, UH(f) is moles of the unsaturated hydrocarbon in the hydrocarbon stream, HUH(f) is the moles of highly unsaturated hydrocarbon in the hydrocarbon stream, and HUH(p) is the moles of the highly unsaturated hydrocarbon in the product.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (for example from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The disclosures of all patents, patent applications, and publications cited herein are hereby incorporated by reference, to the extent that they provide exemplary, procedural or other details supplementary to those set forth herein.

What is claimed is:

1. A system comprising:
  a hydrocarbon stream comprising a highly unsaturated hydrocarbon and carbon monoxide; and
  a reaction zone receiving the hydrocarbon stream, wherein the reaction zone contains at least one hydrogenation catalyst, wherein the highly unsaturated hydrocarbon is hydrogenated in the reaction zone to yield a product comprising an unsaturated hydrocarbon, wherein the at least one hydrogenation catalyst has a selectivity for conversion of the highly unsaturated hydrocarbon to the unsaturated hydrocarbon of about 90 mol % or greater based on the moles of the highly unsaturated hydrocarbon which are converted to the product, wherein the reaction zone comprises a flow index ($I_F$) in a range of about 0.09 to about 35, wherein the $I_F$ is defined as:

$$I_f = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the portion of the reaction zone in units of $ft^3$;

a tube in a furnace fluidly connected to and upstream of the reaction zone;

a cracked gas stream comprising the highly unsaturated hydrocarbon, a saturated hydrocarbon, and carbon monoxide flowing from the tube; and a fractionation zone comprising a deethanizer or a depropanizer fluidly connected to and upstream of the reaction zone, wherein the fractionation zone fractionates the cracked gas stream into an overhead product and a bottoms product, wherein the overhead product comprises the highly unsaturated hydrocarbon, carbon monoxide, and about 90 mol % or greater of the saturated hydrocarbon contained in the cracked gas stream, wherein the overhead product flows to the reaction zone from the fractionation zone via the hydrocarbon stream.

2. The system of claim 1, wherein the selectivity is defined as:

where S is the selectivity in mol %, UH(p) is moles of the unsaturated hydrocarbon in the $$S = 100 \times \left( \frac{UH(p) - UH(f)}{HUH(f) - HUH(p)} \right)$$

product, UH(f) is moles of the unsaturated hydrocarbon in the hydrocarbon stream, HUH(f) is the moles of highly unsaturated hydrocarbon in the hydrocarbon stream, and HUH(p) is the moles of the highly unsaturated hydrocarbon in the product.

3. The system of claim 1,
wherein at least a portion of the tube is made of a co-production metal.

4. The system of claim 3, further comprising:
wherein the co-production metal comprises chromed steel, aluminized steel, or both.

5. The system of claim 4, wherein:
i) the chromed steel is a steel coated with chromium;
ii) the aluminized steel is a steel coated with aluminum;
iii) the chromed steel is an alloy comprising chromium and a steel;
iv) the aluminized steel is an alloy comprising aluminum and a steel; or
v) combinations thereof.

6. The system of claim 1, wherein the [CO] in the reaction zone is from about 0.0001 mol % to about 0.15 mol %.

7. The system of claim 1, wherein the reaction zone comprises a first stage and a second stage, wherein the first stage, the second stage, or both contains the at least one hydrogenation catalyst.

8. The system of claim 7, wherein:
i) the first stage of the reaction zone is a first reactor, wherein the second stage of the reaction zone is a second reactor; or
ii) the first stage of the reaction zone and the second stage of the reaction zone are contained in a common vessel.

9. The system of claim 1, wherein the highly unsaturated hydrocarbon comprises acetylene, wherein the unsaturated hydrocarbon comprises ethylene.

10. The system of claim 1, wherein the highly unsaturated hydrocarbon comprises methylacetylene, propadiene, or both; and wherein the unsaturated hydrocarbon comprises propylene.

11. The system of claim 1, wherein the hydrogenation catalyst comprises palladium, an inorganic support, and optionally, an organophosphorus compound.

12. The system of claim 11, wherein the hydrogenation catalyst further comprises Group 1B metals, Group 1B metal compounds, silver compounds, fluorine, fluoride compounds, sulfur, sulfur compounds, alkali metals, alkali metal compounds, alkaline earth metals, alkaline earth metal compounds, iodine, iodide compounds, or combinations thereof.

13. The system of claim 11, wherein the inorganic support has a surface area of from about 2 $m^2/g$ to about 100 $m^2/g$, and greater than about 90 wt. % of the palladium is concentrated near a periphery of the inorganic support.

14. The system of claim 11, wherein the organophosphorus compound of the hydrogenation catalyst is;
i) present in an amount of from about 0.005 wt. % to about 5 wt. % based on the total weight of the hydrogenation catalyst;
ii) represented by a general formula $(R)_x(OR')_yP=O$, wherein x and y are integers ranging from 0 to 3 and x plus y equals 3, wherein each R is hydrogen, a hydrocarbyl group, or combinations thereof; and wherein each R' is a hydrocarbyl group;
iii) a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group;
iv) a phosphine oxide, a phosphate, a phosphinate, a phosphonate, a phosphine, phosphite, a phosphinite, a phosphonite, or combinations thereof; or
v) combinations thereof.

15. A system comprising:
a furnace comprising at least one tube comprising a co-production metal;
a cracked gas stream comprising a highly unsaturated hydrocarbon, a saturated hydrocarbon, and carbon monoxide flowing from the at least one tube;
a fractionation zone comprising a deethanizer or a depropanizer, wherein the fractionation zone fractionates the cracked gas stream into an overhead product and a bottoms product, wherein the overhead product comprises the highly unsaturated hydrocarbon, carbon monoxide, and about 90 mol % or greater of the saturated hydrocarbon contained in the cracked gas stream;
a hydrocarbon stream comprising the overhead product flowing from the fractionation zone; and
a reaction zone receiving the hydrocarbon stream, wherein the reaction zone comprises at least one hydrogenation catalyst, wherein, in the reaction zone, the highly unsaturated hydrocarbon is hydrogenated to yield a product comprising an unsaturated hydrocarbon in the reaction zone, wherein the reaction zone comprises a flow index ($I_F$) in a range of about 0.09 to about 35, wherein the $I_F$ is defined as:

$$I_f = \frac{F \times [CO]}{V},$$

wherein F is the flow rate of the hydrocarbon stream into the reaction zone in units of kg/h, [CO] is the concentration of carbon monoxide in the hydrocarbon stream in units of mol %, and V is the volume of the portion of the reaction zone in units of $ft^3$.

16. The system of claim 15, wherein the co-production metal comprises chromed steel, aluminized steel, or both.

17. The system of claim 16, wherein:
i) the chromed steel is a steel coated with chromium;
ii) the aluminized steel is a steel coated with aluminum;
iii) the chromed steel is an alloy comprising chromium and a steel;
iv) the aluminized steel is an alloy comprising aluminum and a steel; or
v) combinations thereof.

18. The system of claim 15, wherein the at least one hydrogenation catalyst has a selectivity for conversion of the highly unsaturated hydrocarbon to the unsaturated hydrocarbon of about 90 mol % or greater based on the moles of the highly unsaturated hydrocarbon which are converted to the product, wherein the selectivity is defined as:

$$S = 100 \times \left( \frac{UH(p) - UH(f)}{HUH(f) - HUH(p)} \right)$$

where S is the selectivity in mol %, UH(p) is moles of the unsaturated hydrocarbon in the product, UH(f) is moles of the unsaturated hydrocarbon in the hydrocarbon stream, HUH(f) is the moles of highly unsaturated hydrocarbon in the hydrocarbon stream, and HUH(p) is the moles of the highly unsaturated hydrocarbon in the product.

19. The system of claim 18, wherein the at least one hydrogenation catalyst comprises palladium, an inorganic support, and optionally, an organophosphorus compound.

20. The system of claim 19, wherein the organophosphorus compound of the hydrogenation catalyst is:
i) present in an amount of from about 0.005 wt. % to about 5 wt. % based on the total weight of the hydrogenation catalyst;
ii) represented by a general formula $(R)_x(OR')_yP{=}O$, wherein x and y are integers ranging from 0 to 3 and x plus y equals 3, wherein each R is hydrogen, a hydrocarbyl group, or combinations thereof; and wherein each R' is a hydrocarbyl group;
iii) a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group;
iv) a phosphine oxide, a phosphate, a phosphinate, a phosphonate, a phosphine, a phosphite, a phosphinite, a phosphonite, or combinations thereof; or
v) combinations thereof.

21. The system of claim 15, wherein the [CO] in the reaction zone is from about 0.0001 mol % to about 0.15 mol %.

* * * * *